(12) United States Patent
Caballero-George et al.

(10) Patent No.: US 11,304,965 B2
(45) Date of Patent: *Apr. 19, 2022

(54) FLAVONOID COMPOSITIONS AND RELATED METHODS

(71) Applicant: INSTITUTO DE INVESTIGACIONES CIENTIFICAS Y SERVICIOS DE ALTA TECNOLOGIA (INDICASAT AIP), Clayton (PA)

(72) Inventors: Catherina C. Caballero-George, Panama (PA); Andres Rivera Mondragon, Panama (PA)

(73) Assignee: Instituto de Investigaciones Cientificas y Servicios de Alta Tecnologia, Clayton (PA)

( * ) Notice: Subject to any disclaimer, the term of this patent is extended or adjusted under 35 U.S.C. 154(b) by 0 days.

This patent is subject to a terminal disclaimer.

(21) Appl. No.: 17/083,112

(22) Filed: Oct. 28, 2020

(65) Prior Publication Data

US 2021/0106600 A1    Apr. 15, 2021

Related U.S. Application Data

(63) Continuation of application No. 15/884,118, filed on Jan. 30, 2018, now Pat. No. 10,857,166.

(60) Provisional application No. 62/453,928, filed on Feb. 2, 2017.

(51) Int. Cl.
| | |
|---|---|
| *A61K 31/7016* | (2006.01) |
| *A61K 31/7048* | (2006.01) |
| *A61K 36/185* | (2006.01) |
| *A61P 9/08* | (2006.01) |
| *A61P 9/12* | (2006.01) |
| *A61K 31/216* | (2006.01) |

(52) U.S. Cl.
CPC ........ *A61K 31/7016* (2013.01); *A61K 31/216* (2013.01); *A61K 31/7048* (2013.01); *A61K 36/185* (2013.01); *A61P 9/08* (2018.01); *A61P 9/12* (2018.01); *A61K 2236/15* (2013.01); *A61K 2236/33* (2013.01)

(58) Field of Classification Search
CPC .. C07H 1/08; A61K 31/7016; A61K 31/7048; A61K 36/185
See application file for complete search history.

(56) References Cited

FOREIGN PATENT DOCUMENTS

EP    0 471 584 A1    2/1992

OTHER PUBLICATIONS

Anonymous, "Anti-Eye Bag Effect of a Propylene Glycolic Extract of Cecropia Obtusa Barks in Vivo on Human Volunteers," Research Disclosure, vol. 52, No. 8, Feb. 1, 2006, XP007135880, Kenneth Mason Publications, Hampshire, UK, GB ISSN: 0374-4353.
Sul Xueqin et al., "Analysis of Bioactive Constituents from the Leaves of *Amorpha fruticosa* L.," Journal of Food and Drug Analysis, vol. 25, No. 4, Oct. 2017, pp. 992-999.
Sun Yong et al., "Qualitative and Quantitative Analysis of Phenolics in Tetrastigma Hemsleyanum and their Antioxidant and Antiproliferative Activities," Journal of Agricultural and Food Chemistry, Vo. 61, No. 44, Nov. 2013, pp. 10507-10515.
Toledo, Varenka Martinez et al.; "Genotoxicity testing of Cecropia obtusifolia extracts in two in viva assays: The wing somatic mutation and recombination test of *Drosophila* and the human cytokinesis-block micronucleus test"; Journal of Ethnopharmacology; ScienceDirect;116 (2008); pp. 58-63.
Andrade-Cetto, Adolfo et al.; "Gluconeogenesis inhibition and phytochemical composition of two *Cecropia* species,"; Journal of Ethnopharmacology; 130 (2010); pp. 93-97; Apr. 24, 2010.
Li, Jun et al.; Triterpenoids and flavonoids from Cecropia schreberiana Miq. (Urticaceae), National Institutes of Health; NIH Public Access; Biochem Syst Ecol. Author Manuscript; available in PMC Jun. 1, 2014.
Revilla-Monsalve, Ma. Cristina et al.; "Hypoglycemic effect of Cecropia obtusifolia Bertol aqueous extracts on type 2 diabetic patients,"; Journal of Ethnopharmacology; 111 (2007); pp. 636-640; Jan. 18, 2007.

*Primary Examiner* — Bahar Craigo
(74) *Attorney, Agent, or Firm* — Kory D. Christensen

(57) ABSTRACT

Flavonoids that are isolated from plant material of the genus *Cecropia* can be used to perturb G-protein coupled receptors in a mammalian cell. In some instances, one or more flavonoids may interact with one or more of the G-protein coupled receptors to transiently increase the concentration of cytosolic calcium. Administration of the isolated flavonoids can be used to treat hypertension, to protect the integrity of blood vessels and related conditions.

13 Claims, 21 Drawing Sheets

FLAVONOID COMPOSITIONS AND RELATED METHODS

CROSS-REFERENCE TO RELATED APPLICATIONS

The present application is a continuation of U.S. patent application Ser. No. 15/884,118, filed Jan. 30, 2018, and entitled FLAVONOID COMPOSITIONS AND RELATED METHODS, which claims the benefit of U.S. Provisional Application No. 62/453,928, filed Feb. 2, 2017, both of which hereby incorporated by reference.

TECHNICAL FIELD

The present disclosure relates generally to the field of bioactive compounds. More particularly, some embodiments relate to compositions, formulations, and methods that involve compounds that can be extracted from plants of the genus *Cecropia*, such as flavonoid-containing compositions.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

BACKGROUND

Figure 1:
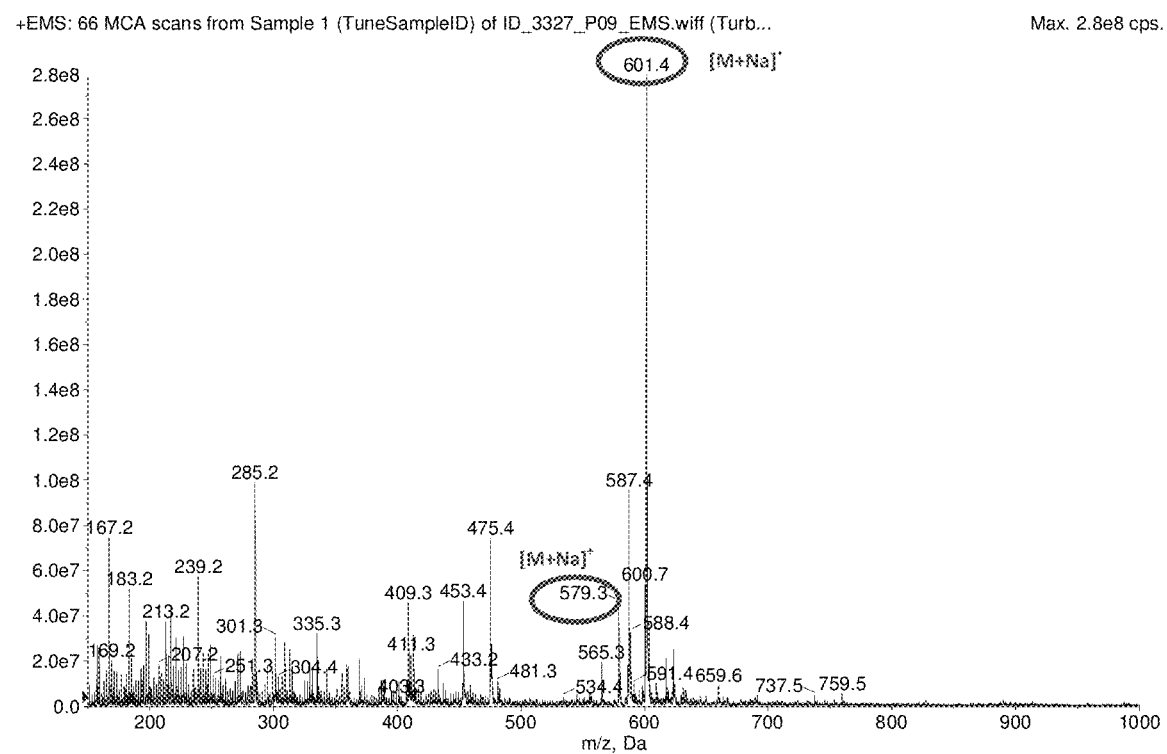
FIG. 1 is an ESI/MS spectrum (positive ion mode) of compound P9 (i.e., isovitexin-2"-O-rhamnoside).

Trees in the genus *Cecropia* (in the Urticaceae family) are generally dioecious, with few branches (usually with a *candelabrum*-like branching system), and a hollow trunk. These trees can have stilt roots, fully amplexicaul stipules, peltate blades with one to two trichilia at the base of the petioles, and inflorescences arranged in digitate clusters (or a single inflorescence), usually enveloped by a spathe until anthesis. In such trees, the interfloral bracts are generally absent, the flowers have two stamens, and the trees have small, dry fruits enveloped by a tubular greenish perianth (Berg et al., Flora 51 Neotrop 1-208 (1990); Berg & Roselli 94 Flora Neotrop. 1-230 (2005)). Trees within this genus are widespread and abundant. For instance, these generally fast-growing trees are distributed across the tropical and subtropical rainforests of Mexico, Central America, and South America at elevations below 2600 m (Franco-Rosselli & Berg, 19 Caldasia 285-296 (1997). The genus includes 61 species (Berg & Roselli 94 Flora Neotrop. 1-230 (2005), including species popularly known, among other folk names, as "yarumo," "guarumo," "guarumbo," "embaúba," "ambay," "torém," and "trumpet tree." (Luengas-Caicedo et al., 62 J Biosci. 701-709 (2007); Costa et al., 22 J Braz Chem Soc. 1096-1102 (2011); Ospina Chávez J, et al., 42 L. Rev Colomb Cienc Quim Farm. 244-259 (2013); Hernández et al., 18 Rev Cuba Plantas Med. 586-595 (2013); Montoya Peláez et al., 23 Brazilian J Pharmacogn. 754-761 (2013).)

Trees within the genus *Cecropia* are of ecological significance. For instance, due to their rapid rate of growth, such trees are often the primary colonizers of deforested tropical areas (Monro et al., available at http://www.kew.org/science/tropamerica/neotropikey/families/Urticacea.htm (2009)) and act as invasive species in non-native regions. (Conn et al., 57 Blumea J Plant Taxon Plant Geogr. 136-142 (2012); GISD, available at http://www.iucngisd.org/gisd/species.php?sc=116.) In addition, most species within the genus *Cecropia* are ant-plants or myrmecophytes. In other words, such trees may live in a mutualistic relationship with a colony of symbiotic ants, especially ants of the genus *Azteca*. They possess specialized structures for offering shelter and food to ants in exchange for protection against natural enemies. (Dejean et al., 97 Naturwissenschaften. 925-934 (2010); Oliveira et al., 10 PLoS One 1-13 (2015).)

Medicinal claims related to the genus *Cecropia* have been advanced in several Latin American countries. Material from such plants has been used as a diuretic, an antioxidant, an antitussive, an expectorant, and for the treatment of several ailments or diseases such as cough, asthma, diabetes, inflammation, anxiety, and depression. (Costa et al., 22 J Braz Chem Soc. 1096-1102 (2011); Gazal et al., 108 Brain Res Bull. 10-17 (2014); Pacheco et al., Biomed Res Int. 1-10 (2014). Reports have also been made purporting the efficacy of plant-derived material in wound healing, pain relief, and antimicrobial activity. Souccar et al., 15 Phytomedicine 462-469 (2008). The therapeutic properties of these plants have generally been attributed to compounds in the plants, such as flavonoids, proanthocyanidins (Luengas-Caicedo et al., 62 J Biosci. 701-709 (2007)), terpenoids, steroids (Ospina Chávez J, et al., 42 L. Rev Colomb Cienc Quim Farm. 244-259 (2013)), chlorogenic- and caffeic acid (Davet et al., 185 J Ethnopharmacol 255-262 (2016)), and other phenolic compounds (Gazal et al., 108 Brain Res Bull. 10-17 (2014)).

Flavonoids are a large group of secondary metabolites. The carbon structure of such compounds can be abbreviated C6-C3-C6, with two aromatic rings and a cycled oxygen. They can be found as aglycones, glycosides, and methyl derivatives at different positions of their core structure. The most abundant flavonoid glycosides are the flavones O/C glycosides and the flavonol O-glycosides. The glycosidic bond is normally found at position 3 or position 7, and the carbohydrate unit can be a glucoside, galactoside, ramnoside, or arabinoside. The biological activities of these compounds can depend not only on the structural differences of the core but also on their glycosylation patterns.

DETAILED DESCRIPTION

This disclosure is related to bioactive compositions, formulations, and methods that involve compounds that can be extracted from plants of the genus *Cecropia*, such as flavonoid compositions.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order of specific steps or actions may be modified.

Amounts, concentrations, and other numerical data may be presented herein in a range format. It is to be understood that such range format is used merely for convenience and brevity and should be interpreted flexibly to include not only the numerical values explicitly recited as the limits of the range, but also all the individual numerical values or subranges encompassed within that range, as if each numerical value and sub-range were explicitly recited. For example, an amount of from 1 mg to 200 mg should be interpreted to include not only the explicitly recited limits of 1 mg and 200 mg, but also individual amounts such as 2 mg, 3 mg, 4 mg, and sub-ranges such as 10 mg to 50 mg, 20 mg to 100 mg, etc. Unless otherwise stated, all ranges include both endpoints.

Some embodiments of the present disclosure relate to methods of perturbing (e.g., acting as an agonist or antagonist for) one or more G-protein coupled receptors in a mammalian cell. In some embodiments, such methods involve obtaining and/or producing a formulation that comprises one or more flavonoids selected from the group consisting of isovitexin-2"-O-rhamnoside, isovitexin-2"-O-glucoside, isovitexin-2"-O-xyloside, isovitexin-O-xyloside, and isoorientin-2"-O-xyloside. Such flavonoid(s) may be derived from plant material of the genus *Cecropia*.

For example, in some embodiments, the formulation is obtained by extracting the one or more flavonoids from plant material of the genus *Cecropia*. In some embodiments, the flavonoids from the plant material are isolated from exclusively (or in greater abundance) from pistillate flowers (female) plants of the genus *Cecropia*. The extraction may be carried out via any suitable solvent. For example, in some embodiment, the solvent used to carry out the extraction may be selected from the group consisting of water, alcohols, ketones, esters, ethers, polyhydric alcohols, chlorine-containing solvents, and mixtures of at least two of the aforementioned solvents. Stated differently, in some embodiments plant material from the *Cecropia* genus may be mixed with one or more solvents to extract a portion of the plant material into the one or more solvents. In some embodiments, the solvent or solvent system is an organic solvent. In some embodiments, the solvent comprises or consists of an alcohol, such as methanol, ethanol, or butanol (e.g., alcohols with four or fewer carbon atoms). The extracted portion of the plant material can be isolated from the remainder of the plant material. Subsequently, at least a portion of the solvent(s) may be removed to obtain a first composition. In some embodiments, the extracted components are further purified (e.g., via chromatography or a fractionated liquid/liquid or liquid/solid extraction technique).

In some embodiments, the plant material from the genus *Cecropia* may be macerated prior to extracting the one or more flavonoids from the plant material. In some embodiments, the plant material is exclusively from aerial parts of the plant (e.g., the leaves and stems) and does not include roots. In some embodiments, the plant material is from one or more plants of the species *Cecropia obtusifolia*.

In some embodiments, the first composition obtained by extraction may be combined with a second composition to form a formulation for administration to mammalian cells and/or a mammalian subject. In some embodiments, the first composition is between 0.001% and 100% of the formulation by weight, between 0.001% and 20% of the formulation by weight, and/or between 0.1% and 3% of the formulation by weight.

In some embodiments, the one or more flavonoids are between 0.1% and 50%, such as between 0.3% and 15% of the formulation by weight. In some embodiments, the formulation includes two or more, three or more, four or more, or all five of the flavonoids selected from the group consisting of isovitexin-2"-O-rhamnoside, isovitexin-2"-O-glucoside, isovitexin-2"-O-xyloside, isovitexin-O-xyloside, and isoorientin-2"-O-xyloside. In some embodiments, the flavonoids of the formulation include or consist of isovitexin-2"-O-xyloside and isovitexin-2"-O-rhamnoside. In some embodiments, the formulation consists essentially of the one or more flavonoids. In other words, the formulation may include one or more flavonoids that are configured to perturb one or more G-protein coupled receptors, but does not include other compounds or substances that materially affect the ability of the formulation to perturb the G-protein coupled receptors. In some embodiments, the formulation consists essentially of isovitexin-2"-O-xyloside and isovitexin-2"-O-rhamnoside. In some embodiments, the formulation includes one or more of a dispersant, a humectant, a carrier, an antistatic agent, a filler, or a diluent. In some embodiments, the formulation includes a total *Cecropia* extract, which includes all active extractable components of the plant. In other embodiments, the extract is further purified to obtain a fraction that includes crude, semi-purified, or purified flavonoids. In some embodiments, only the active components of the extract are used in the formulation.

The formulation may be delivered to one or more mammalian cells to perturb one or more G-protein coupled receptors. In other words, the mammalian cells may be contacted with an effective amount of the formulation. For example, in some embodiments, a cell may be identified in which perturbation of one or more G-protein coupled receptors is desired. For example, in some embodiments, the formulation is delivered to cells in vitro. In other embodiments, the formulation is delivered in an effective amount to a mammalian (e.g., human) patient, such as a patient in which perturbation of G-protein coupled receptor is desired. In some embodiments, such patients may have been selected for treatment based on a diagnosis of high blood pressure or an elevated risk of high blood pressure.

The one or more G-protein coupled receptors that are perturbed by the formulation may be selected from the group consisting of (1) angiotensin II receptor, type 1, (2) angiotensin II receptor, type 2, and (3) endothelin receptor type B. In some embodiments, the one or more flavonoids of the formulation are, individually or collectively, configured to perturb all three of (1) the angiotensin II receptor, type 1, (2) the angiotensin II receptor, type 2, and (3) the endothelin receptor type B. In some embodiments, the formulation acts as an agonist on the $AT_2$ and $ET_B$ receptors, and antagonizes the $AT_1$ receptor. In some embodiments, perturbation of the one or more G-protein coupled receptors causes vasodilation in a mammalian subject. Stated differently, administration of the formulation to a patient may cause a decrease in blood pressure. In other or further embodiments, administration to a patient may provide neuroprotective, cardioprotective, and/or vasculoprotective effects. In some embodiments that include two or more flavonoids, the flavonoids may provide a synergistic effect on the one or more G-protein coupled receptors relative to the same quantity of each of the two or more flavonoids alone.

EXAMPLES

Extraction of Plant Material and Isolation and Characterization of Active Compounds Leaves and stems of dried *Cecropia obtusifolia* were ground to obtain 122.13 g of pulverized plant material. The pulverized plant material was then exhaustively extracted with three liters of methanol. The resulting alcohol extract was washed with 750 ml of hexane and two liters of dichloromethane under agitation. The solvent was then removed under reduced pressure at temperatures of less than 40° C. to afford a dry solid.

The dry alcohol fraction from *C. obtusifolia* (1 g) was submitted to a column chromatography over Sephadex LH-20 (45 cm×1.5 cm i.d, 10 g), using a mobile phase of water:ethanol (1:1). Ten fractions were collected. Fraction 3 and fraction 4 were pooled ("Fraction 3-4") based on their HPLC profile, yielding 308.8 mg of solid material.

The chemical compounds of the solid material from Fraction 3-4 were then isolated by semi-preparative reverse phase liquid chromatography (HPLC) to yield five pure compounds. More particularly, to isolate the chemical compounds of the solid material from Fraction 3-4, the sample was applied using a manual injector and separated on a C18 column (250 mm×10.0 mm i.d.; 5 µm) at 40° C. The mobile phase was a gradient generated by combining solvent A (1% acetic acid, adjusted to pH 3.0) and solvent B (acetonitrile) as follows: 0-30 min, linear gradient from A:B (90:10 v/v) to A:B (85:15 v/v); 30-45 min isocratic A:B (85:15 v/v). The flow rate was 2.0 mL/min. For detection, a chromatogram was recorded at 340 nm using a diode array detector (DAD) while the UV spectrum was monitored over a range of 200-500 nm.

The five compounds that were separated by HPLC were identified based on their mass spectrometry data, nuclear magnetic resonance (NMR) spectrums ($^1$H NMR, $^{13}$C NMR), and by comparison with a reference standard and/or the available literature data. The data used for identification of these compounds is set forth below.

Compound P9

Figure 2:
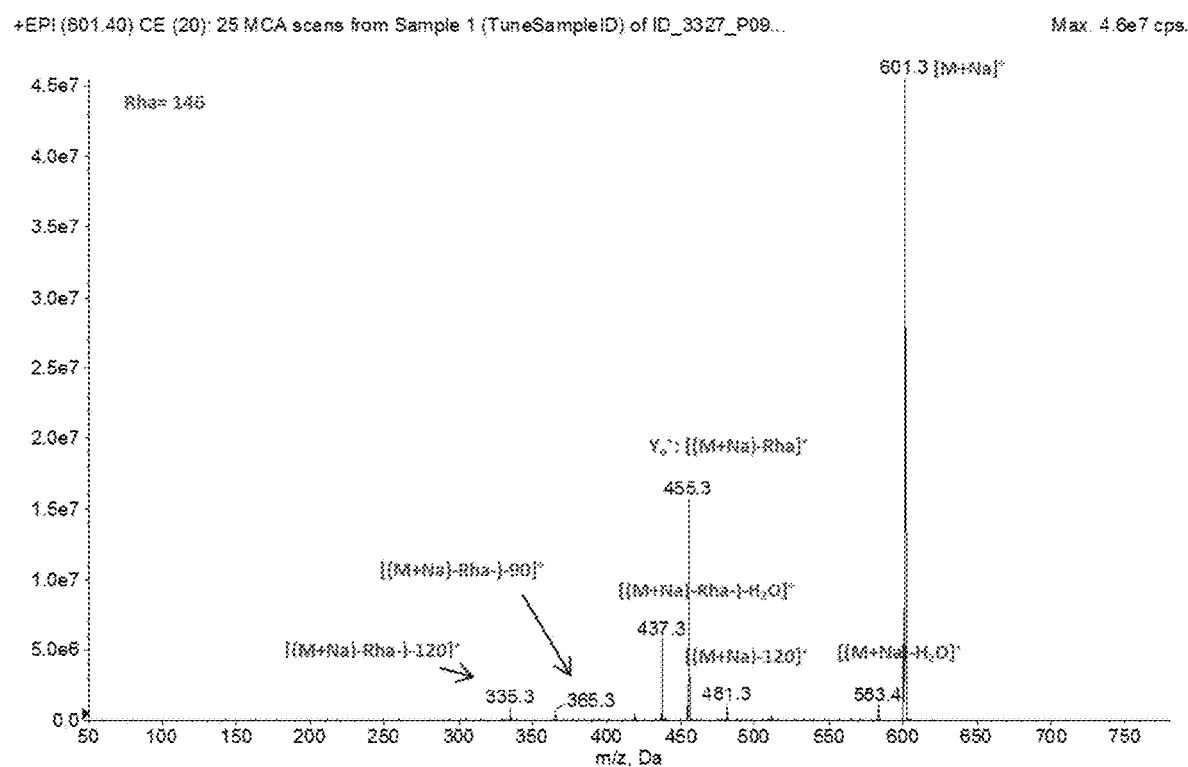
FIG. 2 is an ESI/MS/MS spectrum (positive ion mode) of fragment ion m/z=601 of compound P9.
Figure 3:
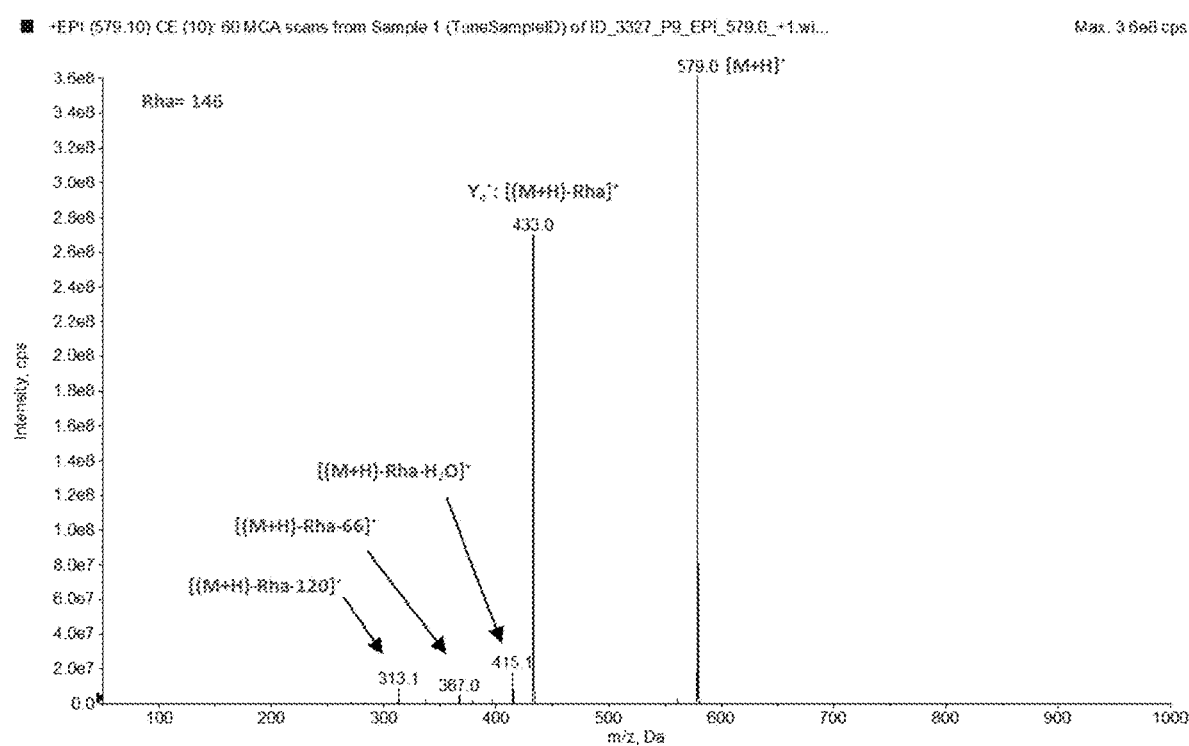
FIG. 3 is an ESI/MS/MS spectrum (positive ion mode) of fragment ion m/z=579 of compound P9.

As shown in both FIG. 1 and Table 1, when subjected to ESI/MS (positive ion mode), compound P9 displayed a molecular ion (MI) at m/z 579.3 $[M+H]^+$ and a base peak (BP) at m/z 601.4 $[M+Na]^+$. Its molecular formula was deduced as $C_{27}H_{30}O_{14}$. Fragmentations of the molecular ion (FIG. 3) and the base peak (i.e., FIG. 2) produced abundant ions $Y_o^+$; 433.0 $[(M+H)-146]^+$ and 455.3 $[(M+Na)-146]^+$. Such masses are attributed to loss of a neutral sugar moiety (deoxyhexose) from glycosylated hydroxyl groups. Ferreres et al., 1161 J Chromatogr A 214-23 (2007); Waridel et al., 926 J Chromatogr A. 29-41 (2001). Ions typical of C-hexosyl flavones (see FIGS. 2-3 and Table 1) were also observed: $^{0,3}X_0^+$: 365.3 $[(M+Na)-146-90]^+$, and $^{0,2}X_0^+$: 335.3 $[(M+Na)-146-120]^+$, and 313.1 $[(M+H)-146-120]^+$ (Ferreres et al., 1161 J Chromatogr A 214-23 (2007); Waridel et al., 926 J Chromatogr A. 29-41 (2001)).

TABLE 1

| | Experimental data | |
|---|---|---|
| No. | ESI(+)-MS | ESI(+)-MS/MS |
| 1 | 601.4 $[M + Na]^+$ | 601.3 $[M + Na]^+$ |
| 2 | | 583.4 $[(M + Na)-H_2O]^+$ |
| 3 | | 481.3 $[(M + Na)-120]^+$ |
| 4 | | 455.3 $[(M + Na)-146 (Rha)]^+ \rightarrow Y_o^+$ |
| 5 | | 437.3 $[(M + Na)-Rha-H_2O]^+$ |
| 6 | | 365.3 $[(M + Na)-Rha-90]^+ \rightarrow {}^{0,3}X_0^+$ |
| 7 | | 335.3 $[(M + Na)-Rha-120]^+ \rightarrow {}^{0,2}X_0^+$ |
| 8 | 579.3 $[M + H]^+$ | 579.3 $[M + H]^+$ |
| 9 | | 433.0 $[(M + H)-146 (Rha)]^+ \rightarrow Y_o^+$ |
| 10 | | 415.1 $[(M + H)-Rha-H_2O]^+$ |
| 11 | | 367.0 $[(M + H)-Glu-66]^+ \rightarrow {}^{2,3}X^+ - 2H_2O$ |
| 12 | | 313.1 $[(M + H)-Rha-120]^+ \rightarrow {}^{0,2}X_0^+$ |

Compound P9 was also characterized by both $^1$H NMR and $^{13}$C NMR. The experimental results are shown in Table 2 alongside published data for isovitexin-2″-O-rhamnoside (Prinz et al., 4 Chem Biodiverse. 2920-31 (2007)).

TABLE 2

| | Experimental data | | Published data Isovitexin-2″-O-rhamnoside (Prinz et al., 4 Chem Biodiverse. 2920-31 (2007)) | |
|---|---|---|---|---|
| No. | $^1$H δ (ppm) DMSO-$d_6$, 400 MHz | $^{13}$C δ (ppm) DMSO-$d_6$, 100 MHz | $^1$H δ (ppm) DMSO-$d_6$, 400 MHz | $^{13}$C δ (ppm) DMSO-$d_6$, 100.6 MHz |
| 2 | | 163.32 | | 163.5 |
| 3 | 6.73 (1H, s) | 102.55 | 6.76 (s) | 102.9 |
| 4 | | 181.99 | | 181.9 |
| 5 | 13.53 (1H, s, OH) | 159.97 | | 160.2 |
| 6 | | 109.17 | | 109.0, 109.6 |
| 7 | | 163.19 | | 162.9 |
| 8 | 6.46 (1H, s) | 93.15 | 6.49 (br. s), 6.48 (br. s) | 93.0, 94.1 |
| 9 | | 156.58, 156.37 | | 156.4 |
| 10 | | 103.43 | | 103.2, 103.9 |
| 1' | | 120.99 | | 121.2 |
| 2' | 7.90 (1H, d, J = 8.78 Hz) | 128.40 | 7.91 (d, J = 8.8) | 128.6 |
| 3' | 6.90 (1H, d, J = 8.78 Hz) | 116.13 | 6.91 (d, J = 8.8) | 116.2 |
| 4' | | 161.39, 161.25 | | 161.4 |
| 5' | 6.90 (1H, d, J = 8.78 Hz) | 116.13 | 6.91 (d, J = 8.8) | 116.2 |

TABLE 2-continued

| | Experimental data | | Published data Isovitexin-2″-O-rhamnoside (Prinz et al., 4 Chem Biodiverse. 2920-31 (2007)) | |
|---|---|---|---|---|
| No. | $^1$H δ (ppm) DMSO-$d_6$, 400 MHz | $^{13}$C δ (ppm) DMSO-$d_6$, 100 MHz | $^1$H δ (ppm) DMSO-$d_6$, 400 MHz | $^{13}$C δ (ppm) DMSO-$d_6$, 100.6 MHz |
| 6' | 7.90 (1H, d, J = 8.78 Hz) | 128.40 | 7.91 (d, J = 8.8) | 128.6 |
| 1″ | 4.64 (1H, d, J = 9.79 Hz) | 71.69 | 4.66 (d, J = 10.2), 4.61 (d, J = 9.5) | 71.0 |
| 2″ | 4.38 (1H, t, J = 9.54 Hz) 4.23 (1H, t, J = 9.54 Hz) | 75.81 76.20 | 4.37 (t, J = 9.0), 4.18 (d, J = 8.8) | 74.4, 75.8 |
| 3″ | 3.34 | 80.11, 79.71 | 3.28-3.38 (m) | 79.7, 79.9 |
| 4″ | 3.16 | 70.01 | 3.05-3.15 (m) | 70.5, 70.9 |
| 5″ | 3.14 | 81.50 | 3.09-3.19 (m) | 81.3 |
| 6″ | 3.41, 3.67 | 61.26, 61.79 | 3.69 (d, J = 11.1), 3.37-4.49 (m) | 61.3, 61.8 |
| 1‴ | 5.04 (1H, d, J = 30.37 Hz) | 100.75, 100.40 | 5.00 (br. s), 5.07 (br. s) | 100.2, 100.6 |
| 2‴ | 3.60 | 70.69 | 3.60 (br. s), 3.31 (br. s) | 70.5 |
| 3‴ | 3.14 | 70.59 | 3.06-3.18 (m) | 70.4 |
| 4‴ | 2.91 (1H, t, 9.16 Hz) | 71.69 | 2.91 (t, J = 8.5), 2.90 (t, J = 8.5) | 71.5 |
| 5‴ | 2.31 (1H, m) | 68.28 | 2.26-2.36 (m) | 68.3 |
| 6‴ | 0.61 (3H, d, J = 5.77 Hz), 0.53 (3H, d, J = 7.03 Hz) | 17.82, 17.60 | 0.51 (d, J = 5.9), 0.59 (d, J = 5.9) | 17.7 |

Since the NMR chemical shifts were in agreement with reported values, Compound P9 was identified as isovitexin-2″-O-rhamnoside.

Compound P9

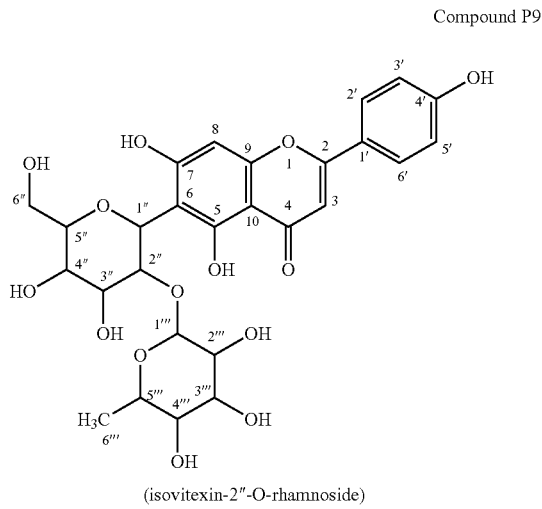 [SMILES: CC1OC(OC2C(c3c(O)cc4oc(-c5ccc(O)cc5)cc(=O)c4c3O)OC(CO)C(O)C2O)C(O)C(O)C1O]

(isovitexin-2″-O-rhamnoside)

Compound P7

Figure 4:
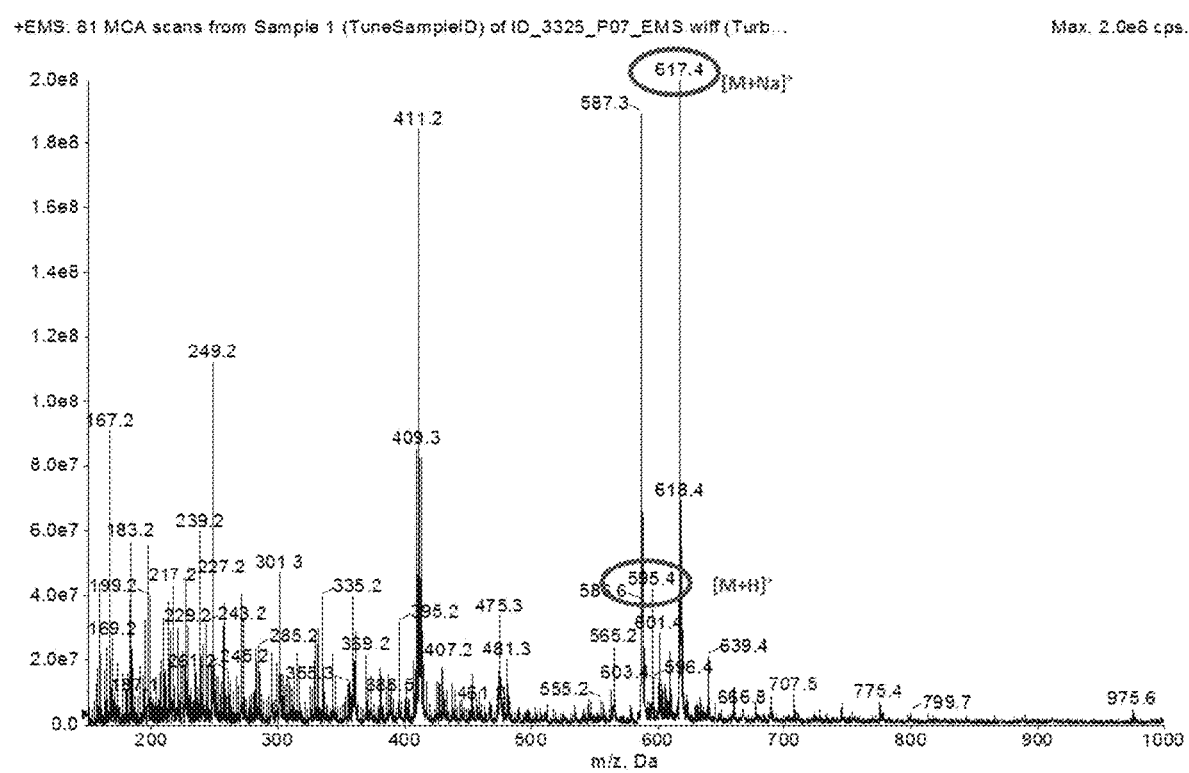
FIG. 4 is an ESI/MS spectrum (positive ion mode) of compound P7 (i.e., isovitexin-2"-O-glucoside).
Figure 5:
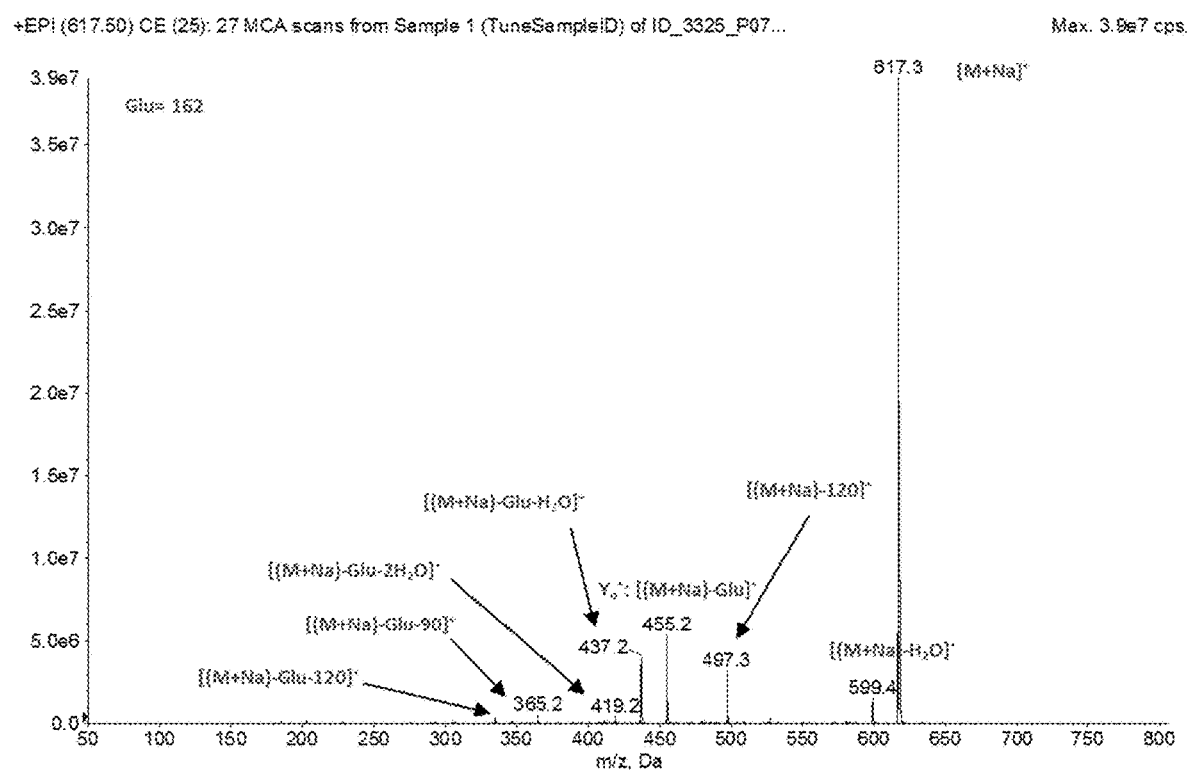
FIG. 5 is an ESI/MS/MS spectrum (positive ion mode) of fragment ion m/z=617 of compound P7.
Figure 6:
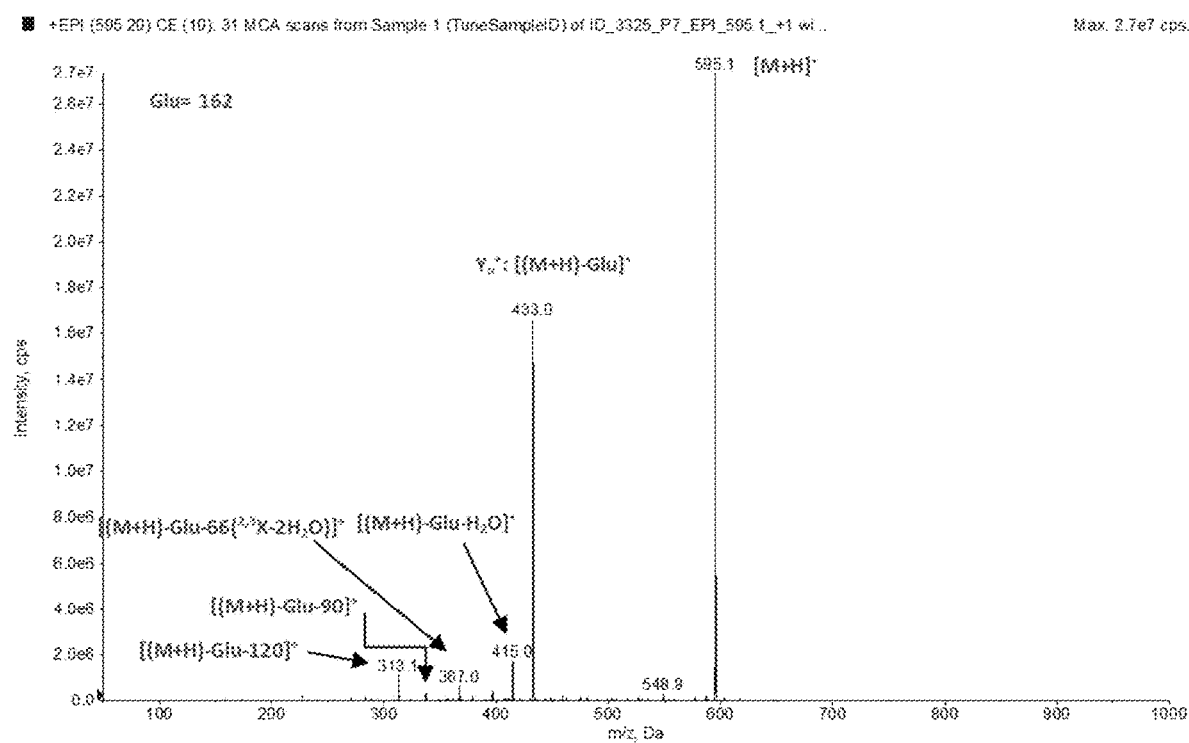
FIG. 6 is an ESI/MS/MS spectrum (positive ion mode) for fragment ion m/z=595 of compound P7.

As shown in FIG. 4, when subject to ESI/MS (positive ion mode), compound P7 displayed a molecular ion (MI) at m/z 595.4 [M+H]$^+$ and a base peak (BP) at m/z 617.4 [M+Na]$^+$. Its molecular formula was deduced as $C_{27}H_{30}O_{15}$. Fragmentations of molecular ion (FIG. 6) and base peak (FIG. 5) produced abundant ions Yo$^+$; 433.0 [(M+H)-146]$^+$ and 455.3 [(M+Na)-162]$^+$. Such masses are attributed to loss of a neutral sugar moiety (hexose) from glycosylated hydroxyl groups (Ferreres et al., 1161 J Chromatogr A 214-23 (2007); Waridel et al., 926 J Chromatogr A. 29-41 (2001)). Ions typical of C-hexosyl flavones (see FIGS. 5-6 and Table 3) were also observed: $^{0.3}X_0^+$: 365.3 [(M+Na)-162-90]$^+$ and 343.0 [(M+H)-162-90]$^+$; and $^{0.2}X_0^+$: 335.3 [(M+Na)-162-120]$^+$ and 313.1 [(M+H)-162-120]$^+$ (Ferreres et al., 1161 J Chromatogr A 214-23 (2007)).

TABLE 3

| | Experimental data | |
|---|---|---|
| No. | ESI(+)-MS | ESI(+)-MS/MS |
| 1 | 617.4[M + Na]$^+$ | 617.3 [M + Na]$^+$ |
| 2 | | 599.4[(M + Na)-H$_2$O]$^+$ |
| 3 | | 497.3[(M + Na)-120]$^+$ |
| 4 | | 455.2[(M + Na)-162 (Glu)]$^+$ → Y$_o^+$ |
| 5 | | 437.2[(M + Na)-Glu-H$_2$O]$^+$ |
| 6 | | 419.2[(M + Na)-Glu-2 H$_2$O]$^+$ |
| 7 | | 365.2[(M + Na)- Glu-90]$^+$ →$^{0.3}X_0^+$ |
| 8 | 595.4 [M + H]$^+$ | 595.1 [M + H]$^+$ |
| 9 | | 433.0[(M + H)-162 (Glu)]$^+$ → Y$_o^+$ |
| 10 | | 415.0[(M + H)- Glu -H$_2$O]$^+$ |
| 11 | | 367.0 [(M + H)- Glu -66]$^+$→$^{2,3}$X$^+$-2H$_2$O |
| 12 | | 313.1 [(M + H)- Glu -120]$^+$ →$^{0.3}X_0^+$ |

Compound P7 was also characterized by $^1$H NMR and $^{13}$C NMR. The $^1$H NMR spectrum shows that a hexose is linked to position 6 (flavone) since H-8 is displayed as a singlet at δ 6.47 ppm. See Table 4 (providing NMR data for compound P7).

TABLE 4

| | Experimental Data | |
|---|---|---|
| No. | $^1$H δ (ppm) DMSO-$d_6$, 400 MHz | $^{13}$C δ (ppm) DMSO-$d_6$, 100 MHz |
| 2 | | 163.31 |
| 3 | 6.77 (1H, s) | 102.72 |
| 4 | | 181.74 |
| 5 | 13.68 (1 OH, br s) 13.55 (1 OH, br s) | 162.31 (HMBC) |
| 6 | | 108.05 |
| 7 | | 163.23 |
| 8 | 6.47 (1H, s) | 93.98, 93.02 |
| 9 | | 156.40 |
| 10 | | 103.42 (HMBC) |
| 1' | | 121.16 |
| 2' | 7.94 (1H, d, J = 8.8 Hz) | 128.43 |
| 3' | 6.93 (1H, d, J = 8.8 Hz) | 116.0 |
| 4' | | 161.19 |
| 5' | 6.93 (1H, d, J = 8.8 Hz) | 116.0 |
| 6' | 7.94 (1H, d, J = 8.8 Hz) | 128.43 |
| 1″ | 4.65 (1H, d, J = 9.8 Hz) | 71.17 |
| 2″ | 4.42 | 81.31 |
| 3″ | 3.42 | 78.58 |
| 4″ | 3.15 | 70.72 |
| 5″ | 3.15 | 81.62 |
| 6″ | 3.68 (1H, d, J = 10.5 Hz), 3.38 | 61.33 |
| 1‴ | 4.11 | 106.3 |
| 2‴ | 2.94 | 74.44 |
| 3‴ | 3.19 | 72.19 |
| 4‴ | 3.19 | 73.36 |

TABLE 4-continued

| | Experimental Data | |
|---|---|---|
| No. | $^1$H δ (ppm) DMSO-$d_6$, 400 MHz | $^{13}$C δ (ppm) DMSO-$d_6$, 100 MHz |
| 5''' | 3.51 | 66.98 |
| 6''' | 3.12, 2.80 | 58.43 |

The HMBC spectra (not shown) of compound P7 indicate that compound P7 has a hexose link through an O-glycosidic bond at position 2". The compound P7 is identified as isovitexin-2"-O-glucoside.

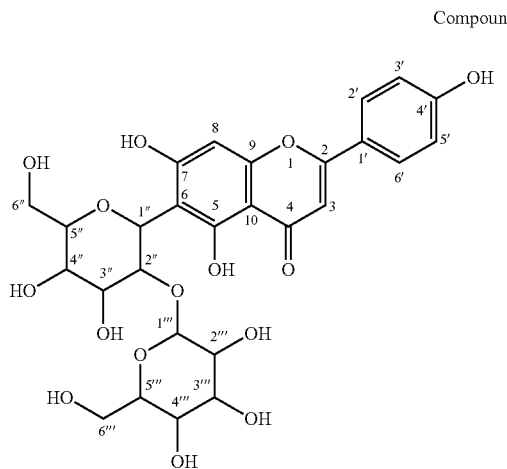

Compound P8

Figure 7:
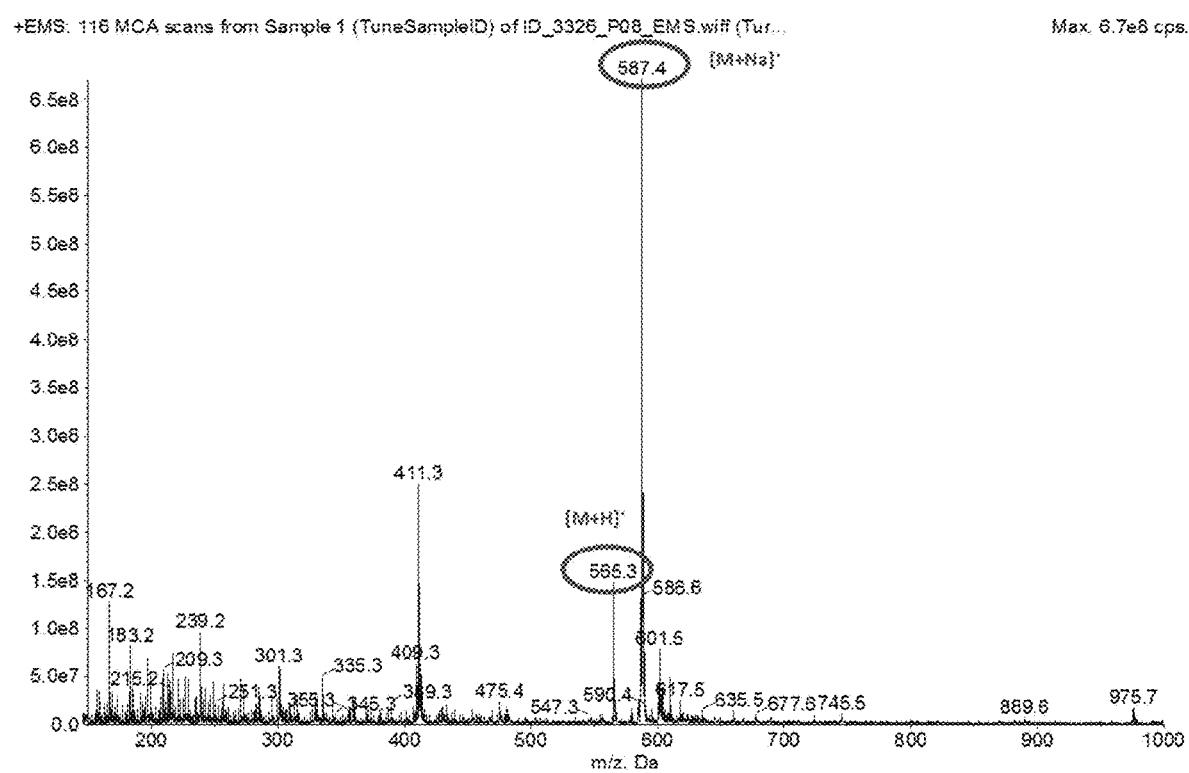
FIG. 7 is an ESI/MS spectrum (positive ion mode) of compound P8 (i.e., isovitexin-2"-O-xyloside).
Figure 8:
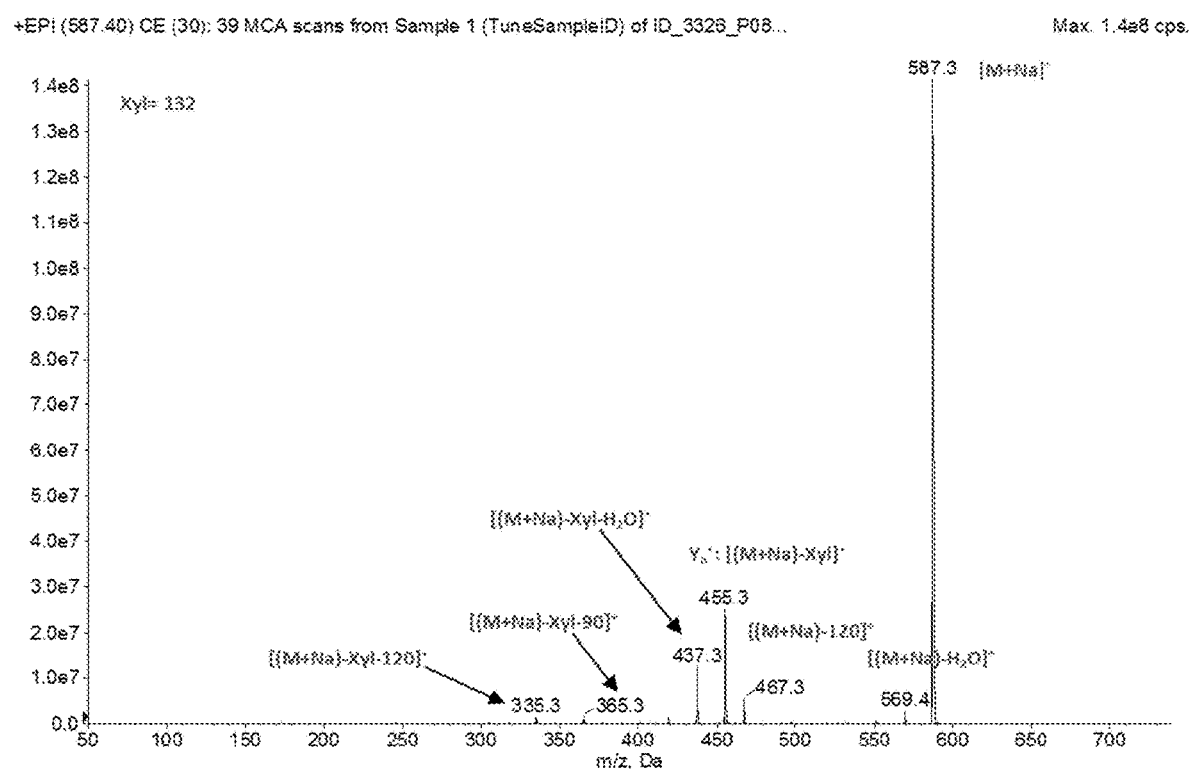
FIG. 8 is an ESI/MS/MS spectrum (positive ion mode) of fragment ion m/z=587 of compound P8.

As shown in FIG. 7, when subject to ESI/MS (positive ion mode), compound P8 displayed a molecular ion (MI) at m/z 565.2 [M+H]$^+$ and a base peak (BP) at m/z 587.3 [M+Na]$^+$. Its molecular formula was deduced as $C_{26}H_{28}O_{14}$. Fragmentations of molecular ion (FIG. 9) produced an abundant ion $Y_o^+$; 433.0=[(M+H)-132]$^+$, which can be attributed to a loss of a neutral sugar moiety (pentose) from glycosylation on hydroxyl groups (Ferreres et al., 1161 J Chromatogr A 214-23 (2007); Waridel et al., 926 J Chromatogr A. 29-41 (2001)). The fragmentation pattern of the base peak is shown in FIG. 8. Ions typical of C-hexosyl flavones (see FIGS. 8-9 and Table 5) were also observed: $^{0,3}X_0^+$: 365.3 [(M+Na)-132-90]$^+$, $^{0,2}X_0^+$: 335.3 [(M+Na)-132-120]$^+$ and 313.1 [(M+H)-132-120]$^+$ (Ferreres et al., 1161 J Chromatogr A 214-23 (2007).

TABLE 5

| | Experimental data | |
|---|---|---|
| No. | ESI(+)-MS | ESI(+)-MS/MS |
| 1 | 587.4[M + Na]$^+$ | 587.3[M + Na]$^+$ |
| 2 | | 569.4[(M + Na)-H$_2$O]$^+$ |
| 3 | | 467.3[(M + Na)-120]$^+$ |
| 4 | | 455.3[(M + Na)-132 (Xyl)]$^+$ →$Y_o^+$ |
| 5 | | 437.3[(M + Na)-Xyl-H$_2$O]$^+$ |
| 6 | | 365.3 [(M + Na)-Xyl-90]$^+$ →$^{0,3}X^+$ |
| 7 | | 335.3 [(M + Na)-Xyl-120]$^+$ → $^{0,2}X^+$ |
| 8 | 565.3 [M + H]$^+$ | 565.3[M + H]$^+$ |
| 9 | | 547.3[(M + H)- H$_2$O]$^+$ |
| 10 | | 433.2[(M + H)-Xyl]$^+$ →$Y_o^+$ |
| 11 | | 415.2[(M + H)-Xyl-H$_2$O]$^+$ |
| 12 | | 397.2[(M + H)-Xyl-2H$_2$O]$^+$ |
| 13 | | 367.2[(M + H)-Xyl-66]$^+$ →$^{2,3}X^+$ -2H$_2$O |
| 14 | | 337.2[(M + H)-Xyl-96]$^+$ →$^{0,4}X^+$-2H$_2$O |
| 15 | | 313.2[(M + H)-Xyl-120]$^+$ → $^{0,2}X^+$ |
| 16 | | 283.2[(M + H)-Xyl-150]$^+$ → $^{0,1}X^+$ |
| 17 | | 271.3[(M + H)-Xyl-Glu]$^+$ |

Figure 9:
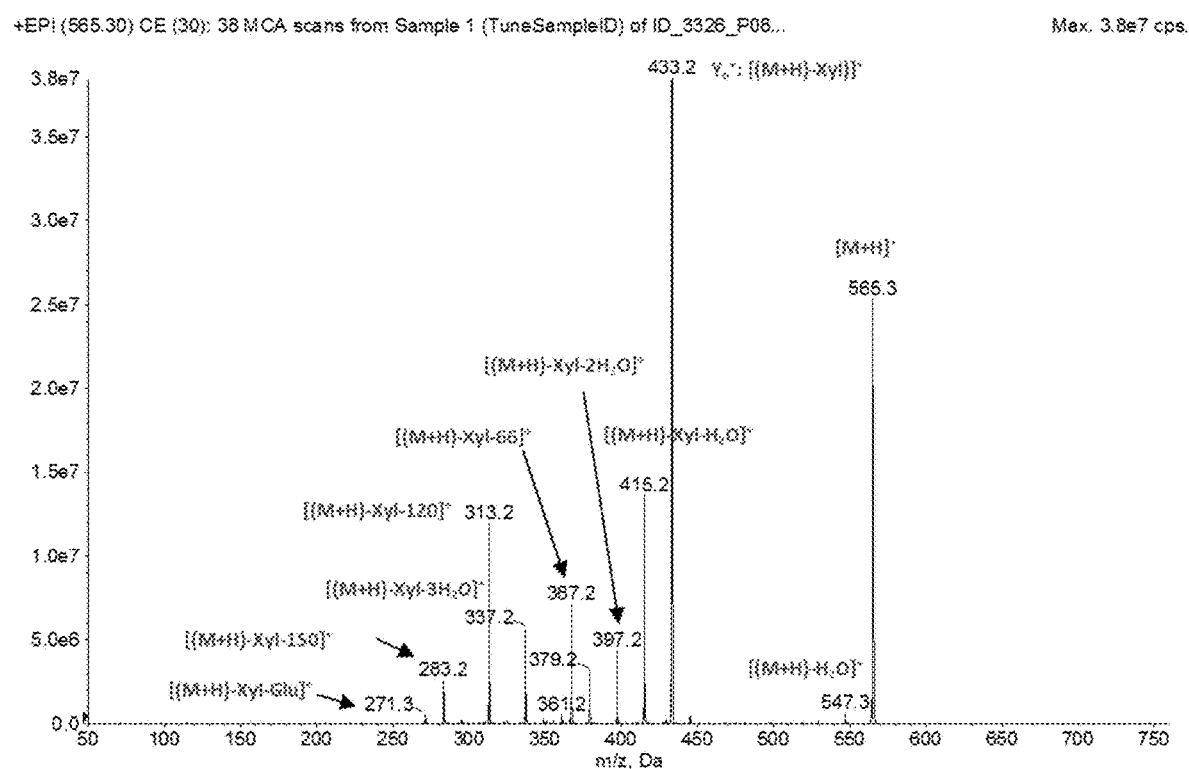
FIG. 9 is an ESI/MS/MS spectrum (positive ion mode) of fragment ion m/z=565 of compound P8.

Additionally, as shown in FIG. 9, compound P8 displayed fragment ions associated to a pentose moiety neutral loss and a hexose cleavage: 415.1 [(M+H)-132-H$_2$O]$^+$, 397.1 [(M+H)-132-2H$_2$O]$^+$, 367.1 [(M+H)-132-66]$^+$→$^{2,3}X^+$→$^{2,3}$H$_2$O, 337.1 [(M+H)-132-96]$^+$→$^{0,4}X^+$-2H$_2$O y 283.1 [(M+H)-132-150]$^+$→$^{0,1}X^+$.

Compound P8 was also characterized by $^1$H NMR and $^{13}$C NMR. The experimental results are shown in Table 6 alongside published date for isovitexin-2"-xyloside (Zielinska-Pisklak et al., 102 J Pharm Biomed Anal 54-63 (2015)).

TABLE 6

| | Experimental data | | Isovitexin 2"-xyloside (Zielińska-Pisklak et al., 102 J Pharm Biomed Anal 54-63 (2015)) | |
|---|---|---|---|---|
| No. | $^1$H δ (ppm) DMSO-$d_6$, 400 MHz | $^{13}$C δ (ppm) DMSO-$d_6$, 100 MHz | $^1$H δ (ppm) DMSO-$d_6$, 300 MHz, 298K | $^{13}$C δ (ppm) DMSO-$d_6$, 750 MHz, 298K |
| 2 | | 163.36 | | 163.44 |
| 3 | 6.74 (1H, s) | 102.73 | 6.78 (1H, s) | 102.69 |
| 4 | | 181.90 | | 181.88 |
| 5 | 13.66, 13.57 (OH) | 162.19 | 13.68 (1H, s, OH) | 160.48 |
| 6 | | 108.17 | | 107.97 |
| 7 | | 162.86 (HMBC H-8) | | 161.74 |
| 8 | 6.45 (1H, s) | 93.82, 93.12 | 6.54 (1H, s) | 93.82 |
| 9 | | 156.45 | | 156.34 |
| 10 | | 103.20 | 10.95 (1H, s, OH) | 103.17 |
| 1' | | 121.11 | | 121.04 |
| 2' | 7.90 (1H, d, J = 8.8 Hz) | 128.45 | 7.93 (1H, d, J = 8.8 Hz) | 128.42 |

TABLE 6-continued

| | Experimental data | | Isovitexin 2"-xyloside (Zielińska-Pisklak et al., 102 J Pharm Biomed Anal 54-63 (2015)) | |
|---|---|---|---|---|
| No. | $^1H$ δ (ppm) DMSO-$d_6$, 400 MHz | $^{13}C$ δ (ppm) DMSO-$d_6$, 100 MHz | $^1H$ δ (ppm) DMSO-$d_6$, 300 MHz, 298K | $^{13}C$ δ (ppm) DMSO-$d_6$, 750 MHz, 298K |
| 3' | 6.91 (1H, d, J = 8.8 Hz) | 116.02 | 6.94 (1H, d, J = 8.8 Hz) | 115.99 |
| 4' | | 161.22 | 10.44 (1H, s, OH) | 161.2 |
| 5' | 6.91 (1H, d, J = 8.8 Hz) | 116.02 | 6.94 (1H, d, J = 8.8 Hz) | 115.99 |
| 6' | 7.90 (1H, d, J = 8.8 Hz) | 128.45 | 7.93 (1H, d, J = 8.8 Hz) | 128.42 |
| 1" | 4.65 (1H, d, 9.8 Hz) | 71.42 | 4.66 (1H, d, J = 9.8 Hz) | 71.23 |
| 2" | 4.38 | 80.22 | 4.42-3.17 (6H, overlapped) | 81.58 |
| 3" | 3.42 | 78.69 | | 78.33 |
| 4" | 3.17 | 70.35 | | 70.35 |
| 5" | 3.17 | 81.62 | | 80.96 |
| 6" | 3.68 (1H, d, 11.54 Hz), 3.39 | 61.52 | | 61.37 |
| 1'" | 4.23 (1H, d, 6.02 Hz) | 105.23 | 4.13 (1H, d, J = 7.2 Hz) | 105.97 |
| 2'" | 3.26 | 72.39 ($^{13}C$) | 3.17-2.57 (5H, overlapped) | 74.18 |
| 3'" | 3.30 | 71.23 | | 76.20 |
| 4'" | 3.42 | 66.58 (66.89 $^{13}C$) | | 69.30 |
| 5'" | 3.02, 2.88 | 64.48 | | 65.67 |

As the NMR chemical shifts were in agreement with reported values (see Table 6), compound P8 was identified as isovitexin-2"-O-xyloside (Zielinska-Pisklak et al., 102 J Pharm Biomed Anal 54-63 (2015).

Compound P8

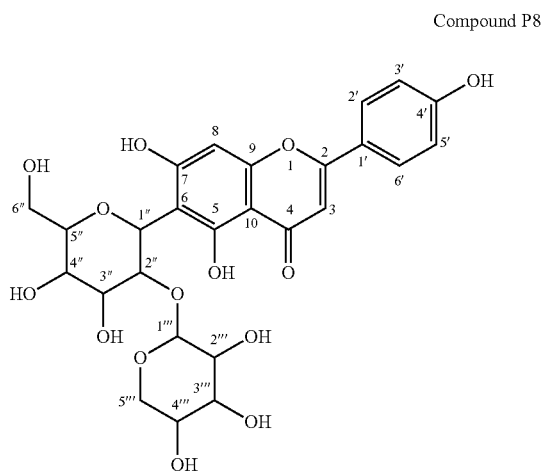 [SMILES: O=c1cc(-c2ccc(O)cc2)oc2cc(O)c(C3OC(CO)C(O)C(O)C3OC3OCC(O)C(O)C3O)c(O)c12]

Compound P6

Figure 10:
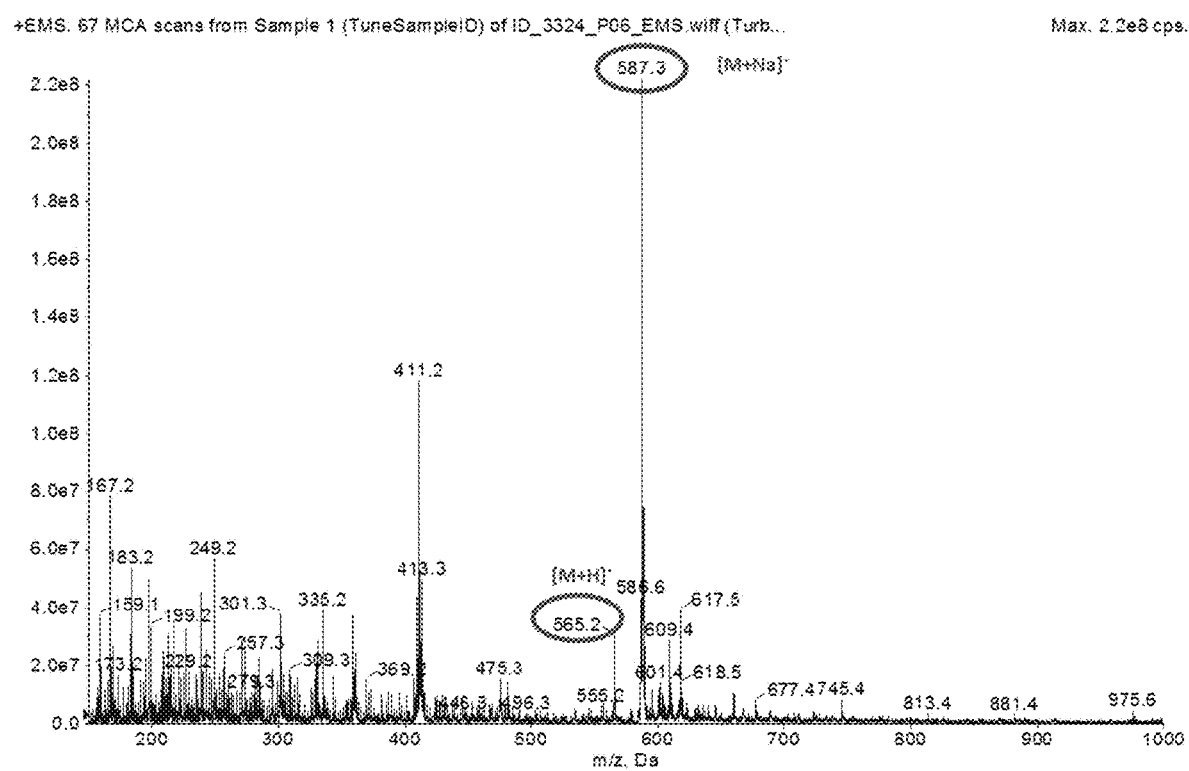
FIG. 10 is an ESI/MS spectrum (positive ion mode) of compound P6 (i.e., isovitexin-O-xyloside).
Figure 11:
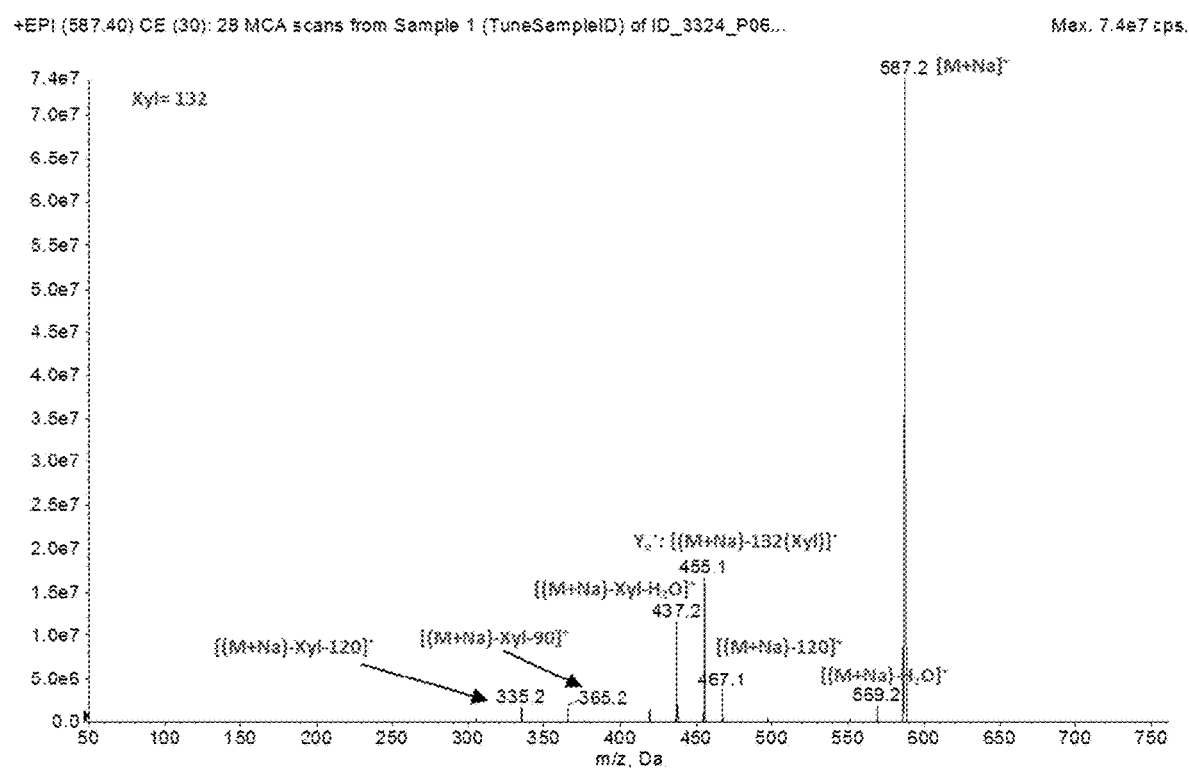
FIG. 11 is an ESI/MS/MS spectrum (positive ion mode) of fragment ion m/z=587 of compound P6.

As shown in FIG. 10 and Table 7, when subjected to ESI/MS (positive ion mode), compound P6 displayed a molecular ion (MI) at m/z 565.2 [M+H]$^+$ and a base peak (BP) at m/z 587.3 [M+Na]$^+$ that closely correspond with values obtained for compound P8. The molecular formula of compound P6 was deduced to be $C_{26}H_{28}O_{14}$. Fragmentations of molecular ion (FIG. 12) produced an abundant ion Yo$^+$; 433.0=[(M+H)-132]$^+$, attributed to loss of a neutral sugar moiety (pentose) from glycosylated on hydroxyl groups (Ferreres et al., 1161 J Chromatogr A 214-23 (2007); Waridel et al., 926 J Chromatogr A. 29-41 (2001)). Ions typical of C-hexosyl flavones (see FIGS. 11 and 12) were also observed: $^{0,3}X_0^+$: 365.3 [(M+Na)-132-90]$^+$, $^{0,2}X_0^+$: 335.3 [(M+Na)-132-120]$^+$ and 313.1 [(M+H)-132-120]$^+$ (Ferreres et al., 1161 J Chromatogr A 214-23 (2007)).

TABLE 7

| | Experimental data | |
|---|---|---|
| No. | ESI(+)-MS | ESI(+)-MS/MS |
| 1 | 587.3[M + Na]$^+$ | 587.2[M + Na]$^+$ |
| 2 | | 569.2[(M + Na)-H$_2$0]$^+$ |
| 3 | | 467.1[(M + Na)-120]$^+$ |
| 4 | | 455.1[(M + Na)-132 (Xyl)]$^+$ |
| 5 | | 437.2[(M + Na)-Xyl-H$_2$0]$^+$ |
| 6 | | 365.2 [(M + Na)-Xyl-90]$^+$ |
| 7 | | 335.2 [(M + Na)-Xyl-120]$^+$ |
| 8 | 565.2 [M + H]$^+$ | 565.2[M + H]$^+$ |
| 9 | | 547.2[(M + H)- H$_2$0]$^+$ |
| 10 | | 445.1[(M + H)-120]$^+$ |
| 11 | | 433.1[(M + H)-Xyl]$^+$ |
| 12 | | 415.1[(M + H)-Xyl-H$_2$0]$^+$ |
| 13 | | 397.1[(M + H)-Xyl-2H$_2$0]$^+$ |
| 14 | | 367.1[(M + H)-Xyl-66]$^+$→$^{2,3}X^+$-2H$_2$O |
| 15 | | 337.1[(M + H)-Xyl-96]$^+$→ $^{0,4}X^+$-2H$_2$O |
| 16 | | 313.1[(M + H)-Xyl-120]$^+$ |
| 17 | | 283.1[(M + H)-Xyl-150]$^+$→ $^{0,1}X^+$ |

Figure 12:
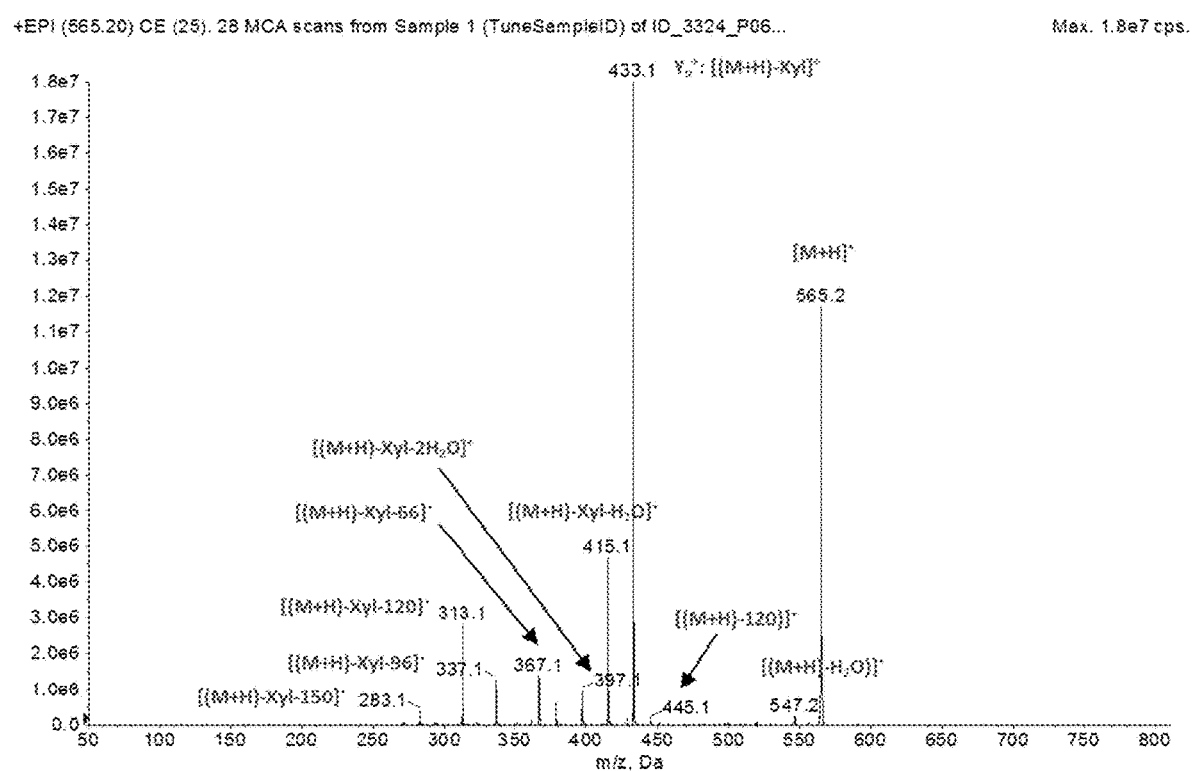
FIG. 12 is an ESI/MS/MS spectrum (positive ion mode) of fragment ion m/z=565 of compound P6.

Additionally, as shown in FIG. 12, compound P6 displayed fragment ions associated to a pentose moiety neutral loss and a hexose cleavage: 415.1 [(M+H)-132-H$_2$O]$^+$, 397.1 [(M+H)-132-2H$_2$O]$^+$, 367.1 [(M+H)-132-66]$^+$→$^{2,3}X^+$-2H$_2$O, 337.1 [(M+H)-132-96]$^+$→$^{0,4}X^+$-2H$_2$O and 283.1 [(M+H)-132-150]$^+$→$^{0,1}X^+$.

Figure 13:
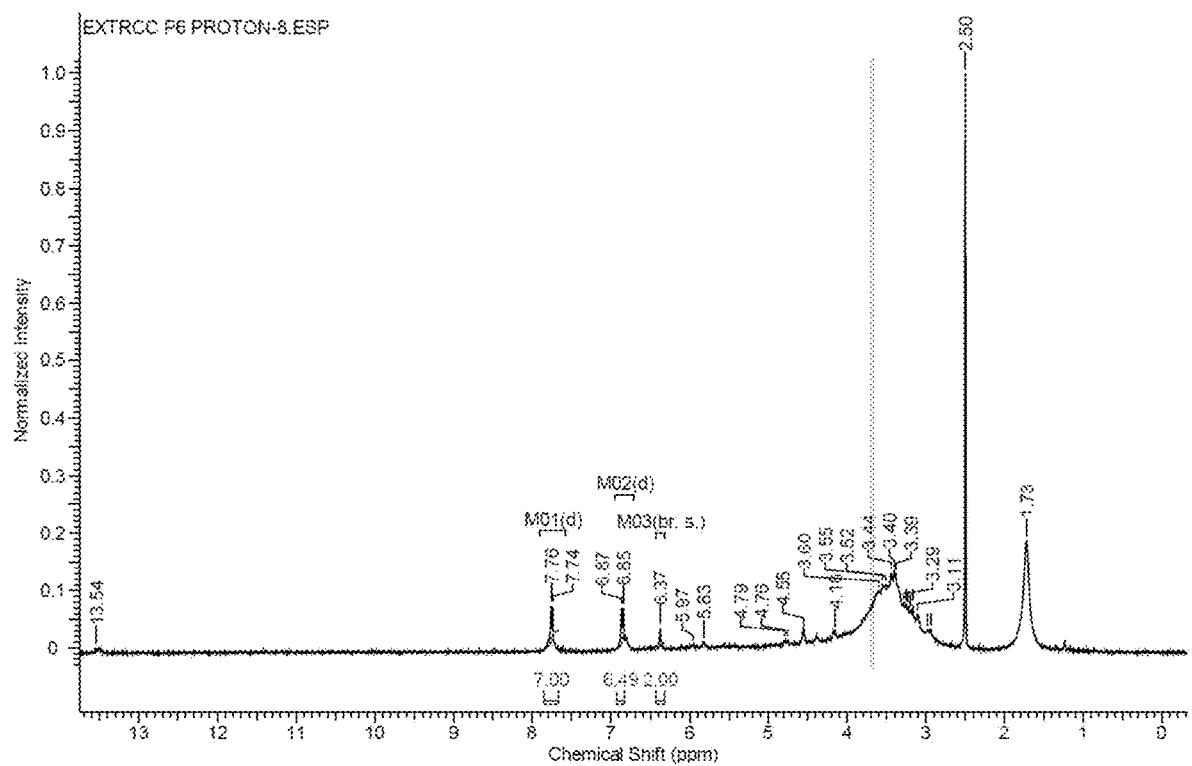
FIG. 13 is a $^1$H NMR spectrum of compound P6.

Compound P6 was also characterized by both $^1H$ NMR. The experimental results are shown in FIG. 13 and Table 8.

TABLE 8

Experimental data
$^1$H δ (ppm) DMSO-$d_6$, 400 MHz

| No. | Compound P6 | Compound P8 |
|---|---|---|
| 3 | 6.81 (1H, s) | 6.74 (1H, s) |
| 5 | 13.54 (1H, br s, OH) | 13.66, 13.57 (OH) |
| 8 | 6.37 (1H, s) | 6.45 (1H, s) |
| 2' | 7.77 (1H, d, J = 8.7 Hz) | 7.90 (1H, d, J = 8.8 Hz) |
| 3' | 6.85 (1H, d, J = 8.7 Hz) | 6.91 (1H, d, J = 8.8 Hz) |
| 5' | 6.85 (1H, d, J = 8.7 Hz) | 6.91 (1H, d, J = 8.8 Hz) |

TABLE 8-continued

Experimental data
$^1$H δ (ppm) DMSO-$d_6$, 400 MHz

| No. | Compound P6 | Compound P8 |
|---|---|---|
| 6' | 7.77 (1H, d, J = 8.7 HZ) | 7.90 (1H, d, J = 8.8 Hz) |
| 1" | 4.66 | 4.65 (1H, d, 9.8 Hz) |
| 2" | 4.39 | 4.38 |
| 3" | 3.44 | 3.42 |
| 4" | 3.17 | 3.17 |
| 5" | 3.20 | 3.17 |
| 6" | * | 3.68 (1H, d, 11.54 Hz), 3.39 |
| 1''' | 4.16 | 4.23 (1H, d, 6.02 Hz) |
| 2''' | * | 3.26 |
| 3''' | * | 3.30 |
| 4''' | * | 3.42 |
| 5''' | * | 3.02, 2.88 |

Note:
* No identified chemical shifts.

The $^1$H NMR spectrum displayed similar chemical shifts to compound P8. These results suggest that compound P6 is an isomer of compound P8. Accordingly, compound P6 is identified as isovitexin-O-xyloside.

Compound P4

Figure 14:
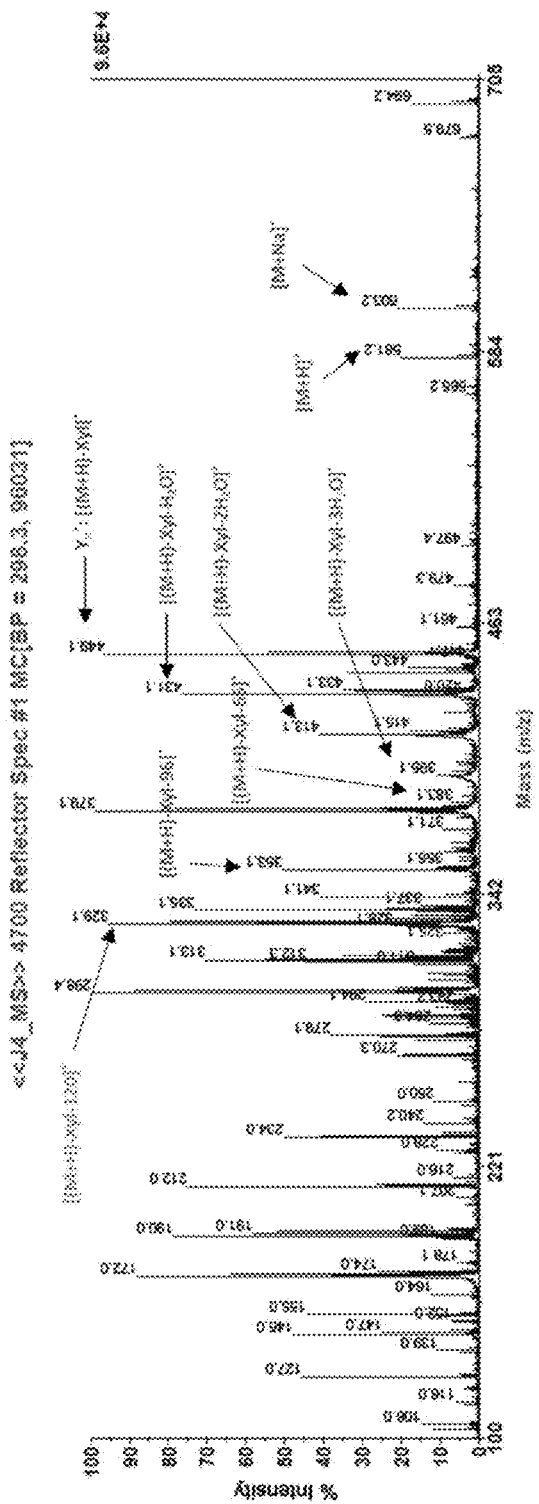
FIG. 14 is a MALDI/TOF spectrum (positive ion mode) of compound P4 (i.e., isoorientin-2"-O-xyloside).
Figure 15:
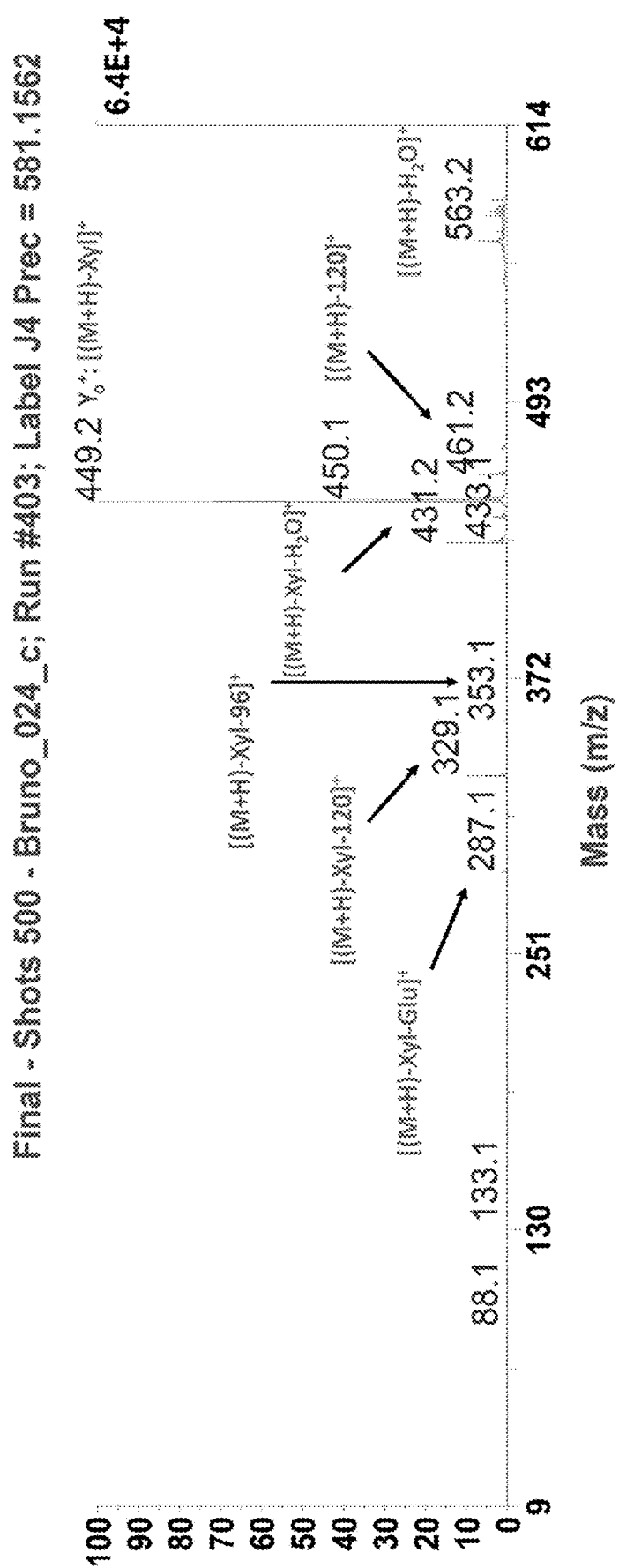
FIG. 15 is a MALDI/MS/MS spectrum (positive ion mode) of fragment ion m/z=581 of compound P4.
Figure 16:
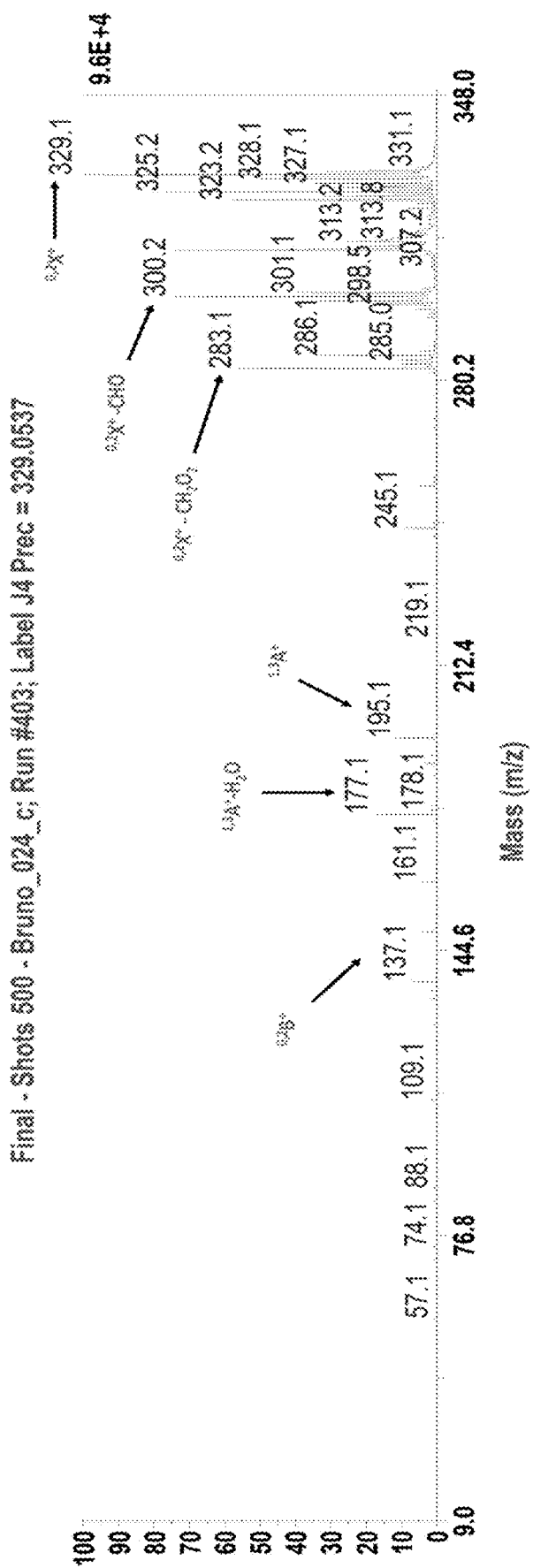
FIG. 16 is a MALDI/TOF/TOF spectrum (positive ion mode) of fragment ion m/z=329 of compound P4.

As shown in both FIG. 14 and Table 9, when subjected to ESI/MS (positive ion mode) compound P4 displayed a molecular ion (MI) at m/z 581.2 [M+H]$^+$ and a base peak (BP) at m/z 603.2 [M+Na]$^+$. Its molecular formula was deduced as $C_{26}H_{28}O_{15}$. Fragmentation of molecular ion (FIG. 15) produced an abundant ion Yo$^+$; 449.2=[(M+H)−132]$^+$, which was attributed to loss of a neutral sugar moiety (pentose) from glycosylated hydroxyl groups (Ferreres et al., 1161 J Chromatogr A 214-23 (2007); Waridel et al., 926 J Chromatogr A. 29-41 (2001)). As shown in Table 9 and FIGS. 15 and 16, ions typical of C-hexosyl flavones were also observed: $E_1$: 431.1 [(M+H)-Xyl-H$_2$O]$^+$, $E_2$: 413.1 [(M+H)-Xyl-2H$_2$O]$^+$, $E_3$: 395.1 [(M+H)-Xyl-3H$_2$O]$^+$, $^{2,3}$X+-2H$_2$O: 383.1 [(M+H)-Xyl-66]$^+$, $^{0,4}$X-2H$_2$O: 353.1 [(M+H)-Xyl-96]$^+$ and $^{0,2}$X$^+$: 329.1 [(M+H)-Xyl-120]$^+$ (Ferreres et al., 1161 J Chromatogr A 214-23 (2007).

TABLE 9

Experimental data

| No. | MALDI(+)-MS | MALDI(+)-MS/MS |
|---|---|---|
| 1 | 603.2 [M + Na]$^+$ | 581.2 [M + H]$^+$: |
| 2 | 581.2 [M + H]$^+$ | a. 563.2[(M + H)-H$_2$O]$^+$ |
| 3 | 449.1[(M + H)-132 (Xyl)]$^+$→ Y$_o^+$ | b. 461.2[(M + H)-120]$^+$ →$^{0,2}$X$^+$ |
| 4 | 431.1 [(M + H)- Xyl -H$_2$O]$^+$ | c. 449.2[(M + H)-132 (Xyl)]$^+$→ Y$_o^+$ |
| 5 | 413.1 [(M + H)- Xyl -2H$_2$O]$^+$ | d. 431.2 [(M + H)- Xyl -H$_2$O]$^+$ |
| 6 | 395.1 [(M + H)-Xyl -3H$_2$O]$^+$ | e. 353.1 [(M + H)-Xyl-96]$^+$→ ($^{0,4}$X-2H$_2$O)$^+$ |
| 7 | 383.1[(M + H)-Xyl-66]$^+$→ ($^{2,3}$X+-2H$_2$O) | f. 329.1[(M + H)-Xyl-120]$^+$ → $^{0,2}$X$^+$ |
| 8 | 353.1 [(M + H)-Xyl-96]$^+$→ ($^{0,4}$X-2H$_2$O)$^+$ | g. 287.1[(M + H)-Xyl-Glu]$^+$ |
| 9 | 329.1 [(M + H)-Xyl-120]$^+$ → $^{0,2}$X$^+$ | |
| | | 329.1 [(M + H)-Xyl-120]$^+$→$^{0,2}$X$^+$ |
| | | a. 329.1: $^{0,2}$X$^+$ |
| | | b. 300.2: $^{0,2}$X$^+$ - CHO |
| | | c. 283.1: $^{0,2}$X$^+$ - CH$_2$O$_2$ |
| | | d. 195.1: $^{1,3}$A$^+$ |
| | | e. 177.1: $^{1,3}$A$^+$ - H$_2$O |
| | | f. 137.1: $^{0,2}$B$^+$ |

Compound P4 was also characterized by $^1$H NMR. The experimental results are shown in Table 10 alongside published data for isoorientin-2"-O-xyloside (Matsuzaki et al., 44 Japanese Soc Pharmacogn 251-253 (1990)).

TABLE 10

| No. | Experimental data $^1$H δ (ppm) DMSO-d 400 MHz | Published data Isoorientin-2"-O-xyloside (Matsuzaki et al., 44 Japanese Soc Pharmacogn 251-253 (1990)) $^1$H δ (ppm) DMSO-d 400 MHz |
|---|---|---|
| 3 | 6.65 (1H, s) | 6.68 (1H, s) |
| 5 | 13.55 (1H, br. s, OH) | 13.70 (1H, br. s, OH) |
| 8 | 6.43 (1H, s) | 6.46 (1H, s) |
| 7 | — | — |
| 2' | 7.39 (1H, d, J = 2.5 Hz) | 7.40-7.43 (1H, m) |
| 3' | — | — |
| 4' | — | — |
| 5' | 6.87 (1H, d, J = 2.1 Hz) | — |
| 6' | 7.42 (1H, d, J = 2.1 Hz) | 7.40-7.43 (1H, m) |
| 1" | 4.63 (1H, d, J = 9.79 Hz) | 4.64 (1H, d, J = 9.6 Hz) |
| 2" | * | — |
| 3" | * | — |
| 4" | * | — |

TABLE 10-continued

| | Experimental data $^1$H δ (ppm) DMSO-d | Published data Isoorientin-2″-O-xyloside (Matsuzaki et al., 44 Japanese Soc Pharmacogn 251-253 (1990)) $^1$H δ (ppm) |
|---|---|---|
| No. | 400 MHz | DMSO-d 400 MHz |
| 5″ | * | — |
| 6″ | * | — |
| 1‴ | 4.11 (1H, d, , J = 6.02 Hz) | 4.12 (1H, d, J = 6.7 Hz) |
| 2‴ | * | — |
| 3‴ | * | — |
| 4‴ | * | — |
| 5‴ | * | — |

Note:
* No identified chemical shifts.
— Not reported

The $^1$H NMR spectrum shows that a hexose is attached to position 6 of the flavone since H-8 appeared as a singlet at δ 6.43 ppm (Matsuzaki et al., 44 Japanese Soc Pharmacogn 251-253 (1990)). In addition, 5-OH is displayed as a broad singlet at δ 13.49 ppm (Doyama et al., 96 J Ethnopharmacol 371-4 (2005); Wen et al., 2 Asian J Tradit Med. 149-53 (2007)). The compound P4 is identified as isoorientin-2″-O-xyloside.

Compound P4

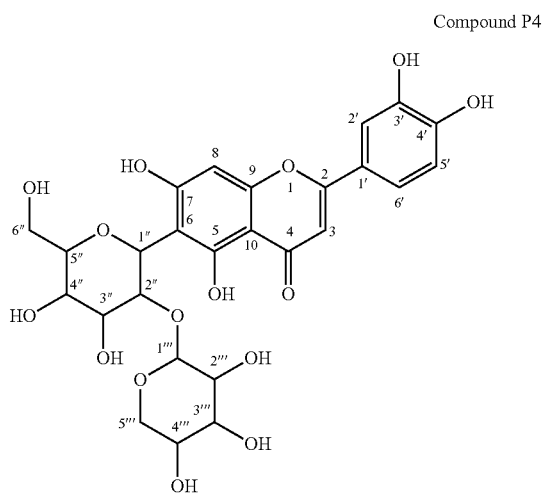 [SMILES: O=c1cc(-c2ccc(O)c(O)c2)oc2cc(O)c(C3OC(CO)C(O)C(O)C3OC3OCC(O)C(O)C3O)c(O)c12]

Compound P2

Figure 17:
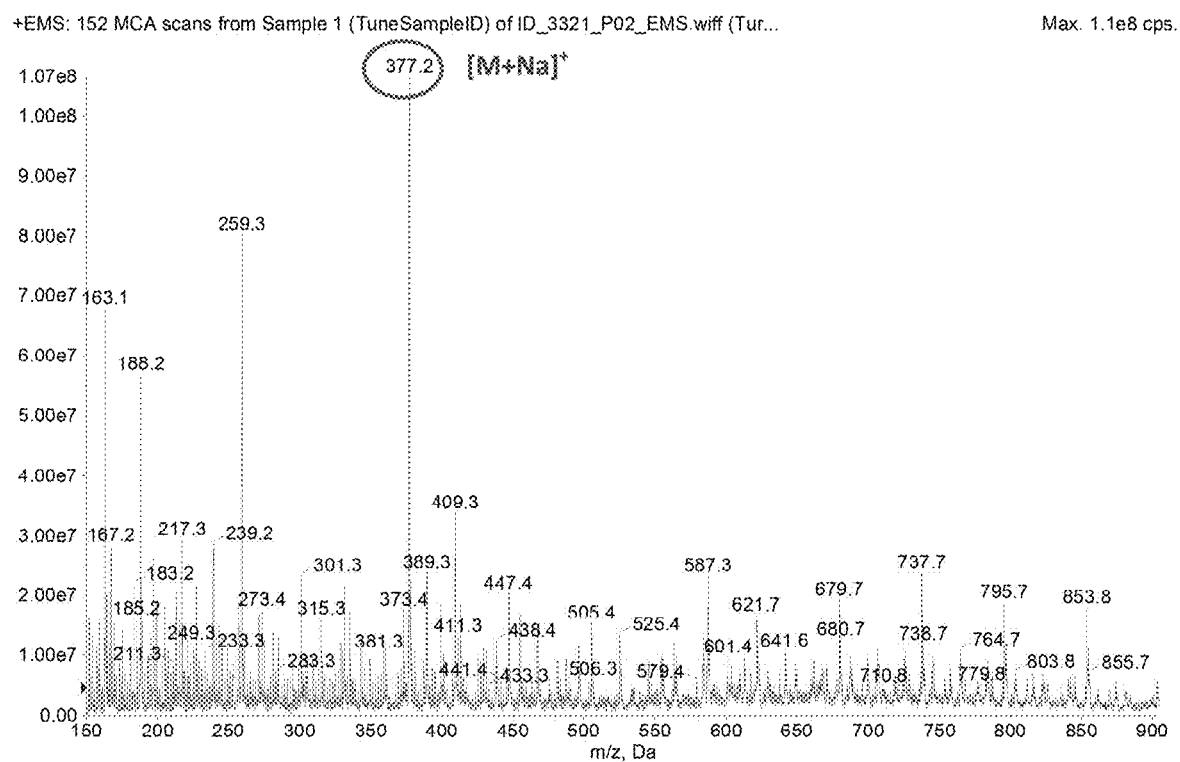
FIG. 17 ESI/MS spectrum (positive ion mode) of compound P2 (i.e., chlorogenic acid)
Figure 18:
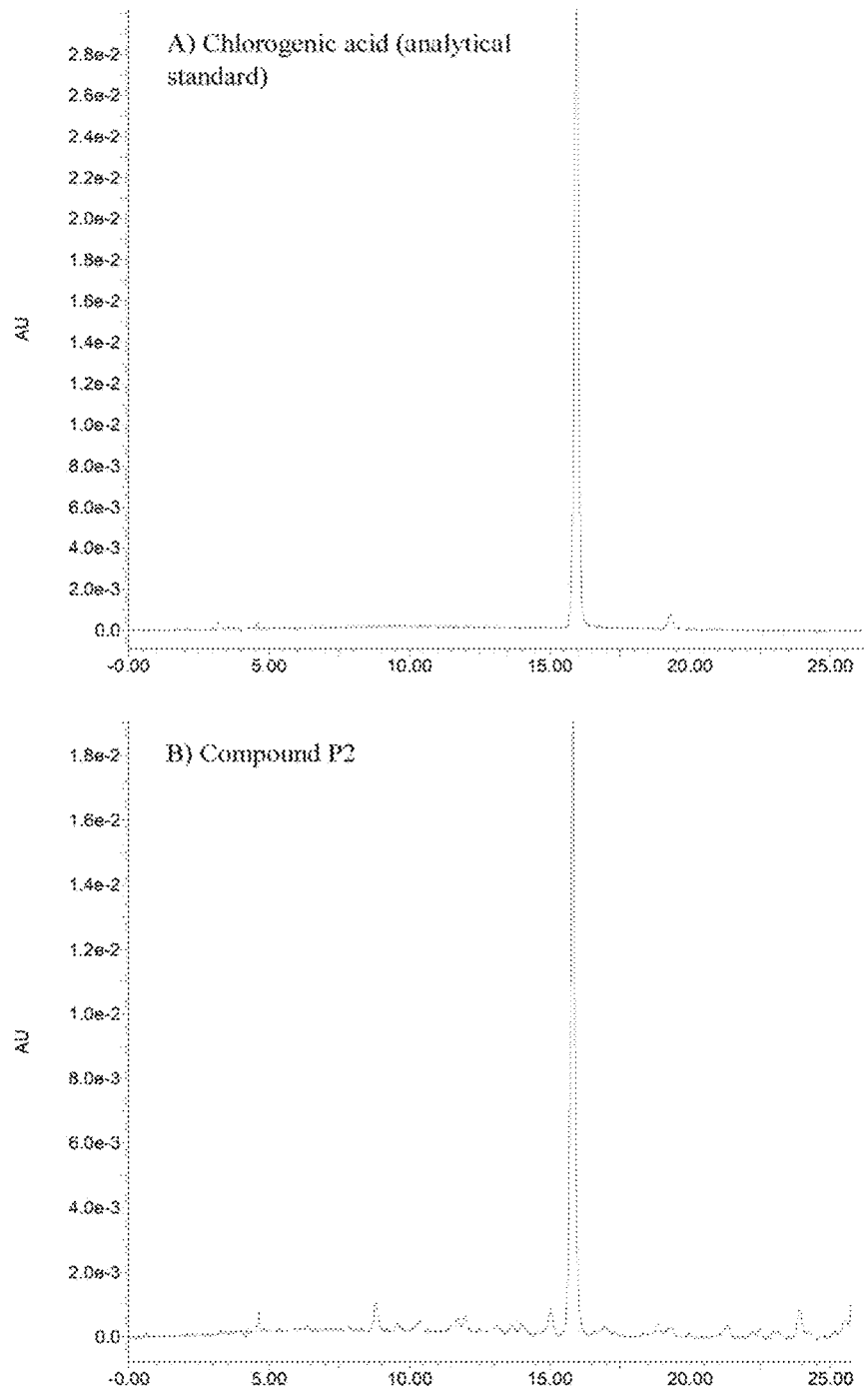
FIG. 18 is an UV chromatogram of chlorogenic acid and compound P2.

As shown in FIG. 17, when subjected to ESI/MS (positive ion mode), compound P2 displayed a base peak (BP) at m/z 377.2 [M+Na]$^+$. Its molecular formula was deducted as $C_{16}H_{18}O_9$. The compound P2 is identified as chlorogenic acid by direct comparison (retention time) with an analytical standard (FIG. 18).

Compound P2

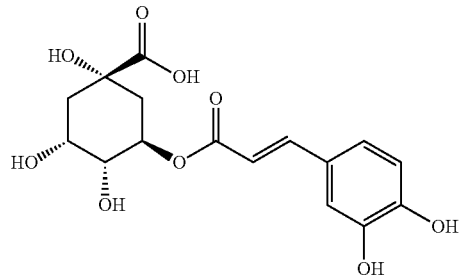

Perturbation of G-Protein Coupled Receptors

Angiotensin II, receptor type 1 ("AT$_1$"), angiotensin II, receptor type 2 ("AT$_2$"), and endothelin receptor type B ("ET$_B$") are G-protein coupled receptors that play a role in blood pressure regulation and vascular remodeling. Activation of the AT$_1$ receptor can lead to vasoconstriction, aldosterone synthesis and secretion, increased vasopressin secretion, cardiac hypertrophy, augmentation of peripheral noradrenergic activity, vascular smooth muscle cells proliferation, decreased renal blood flow, renal renin inhibition, renal tubular sodium reuptake, modulation of central sympathetic nervous system activity, cardiac contractility, central osmocontrol, and extracellular matrix formation (Catt et al., J Cardiovasc Pharmacol. 6 Suppl 4:S575-86 (1984). Activation of the AT$_2$ receptor can induce vasodilation in multiple vascular beds, enhance natriuresis, prevent vascular remodeling by decreasing collagen deposition, and attenuate arterial stiffening. Activation of the ET$_B$ receptor can lead to vasodilation and clearance of endothelin 1 from the systemic blood.

To investigate the vasculoprotective, neuroprotective, and/or antihypertensive properties of Cecropia extracts, Chinese hamster ovary cells that had been stably transfected with aequorin (CHO-AEQ cells) were transiently transfected with various G-protein coupled receptors.

More particularly, CHO-AEQ cells were cultured in Dulbecco's Modified Eagle's Medium (DMEM) containing 10% fetal bovine serum as previously described (Vanderheyden et al., 126 Br J Pharmacol 1057-1065 (1999)). At 75% confluency, these cells were transiently transfected with pcDNA3.1+ plasmid DNA into which had been inserted the coding region for human AT$_1$, AT$_2$, or ET$_B$ receptor. The transient transfection was performed with Fugene HD® following the manufacturers' instructions (2 μg DNA to 7 μl Fugene HD® in Opti-MEM® medium. After transfection, the cells were cultured for an additional day, after which they were harvested and loaded with coelenterazine-h.

Intracellular calcium can be detected based on the interaction of calcium ions with the calcium binding bioluminescent complex aequorin. Upon calcium binding, aequorin oxidizes coelenterazine-h into coelenteramide with production of $CO_2$ and emission of light (466 nm) (Le Poul et al., 7 J Biomol Screen 57-65 (2002). The CHO-AEQ cells that had been transiently transfected with human AT$_1$, human AT$_2$ or human ET$_B$ receptors were used in a bioluminescence assay to evaluate whether—and to what extent—material isolated from Cecropia obtusifolia could perturb G-protein coupled receptor(s).

Confluent CHO-AEQ cells that were grown and transfected in 75 cm$^2$ culture flasks were harvested by a brief treatment with a trypsin/EDTA solution, centrifuged, and resuspended in DMEM-F12 cell culture medium containing 0.1% BSA and denoted as assay buffer, at a cell density of $2.5 \times 10^6$ cells/ml. Subsequently, coelenterazine-h was added to the cell suspension to a final concentration of 5 µM. Cells were then incubated between 14 h and 18 h at room temperature in the dark under gentle shaking. After this loading step, 15 ml of assay buffer was added to the cells and then centrifuged for 7 min at 1100 rpm in a swinging bucket centrifuge. The resulting cell pellets were gently resuspended in assay buffer containing 1 µM coelenterazine-h at a cell density of $5 \times 10^5$ cells/ml. After a further incubation of 1.5 h at room temperature, the cell suspension was distributed at 100 µl/well in white Cellstar 96-well plates.

To assess the activity of the compounds derived from *Cecropia obtusifolia* extracts, lyophilized crude extract (and compounds that had been identified in the extract) were dissolved in DMSO at 1 mg/ml, and then further diluted in assay buffer to 100 µg/ml (final concentration) (Caballero-George et al., 4 Curr. Trends Biotechnol Pharm 881-899 (2010)). A 50 aliquot was then added to each well containing the transiently transfected cells. For comparison, control peptides were diluted in assay buffer to a final concentration of 0.1 µM angiotensin II or 10 nM endothelin-1. These control peptides are known to cause a transient rise in cytosolic calcium. The agonist solutions were loaded in the cell injector of a Victor spectrophotometer, and a 96-well plate was inserted.

Measurements were initiated by injecting 50 µl solution/well, and the bioluminescence was recorded every 200 ms for 120 cycles. To account for slight variations in cell number, a final concentration of 10 µM ATP was added by a second injector to the cells (50 µl/well) and the resulting response was measured.

The effects were quantified by calculation of the area under the curves by integration of the obtained transient responses using GraphPad Prism 5™. The activation of the $AT_1$, $AT_2$, or $ET_B$ receptors was expressed as a fractional response. This is obtained by dividing the agonist response by the sum of the agonist and ATP response for each well (i.e., agonist response/(ATP+agonist response)). The fractional response is used to normalize the agonist response in each well for the amount of living cells in the well (that is proportional to the ATP response) (Nikolaou 35 al., 702 Eur J Pharmacol 93-102 (2013)).

The effect of the evaluated extracts was calculated as percent inhibition of the control responses and is given as the average±standard error of three determinations. In order to validate the three receptor assays, the agonist responses were measured after pre-incubation with 0.1 µM BQ788 or 100 µM losartan, which are selective antagonists for the $AT_2$, $ET_B$, and $AT_1$ receptors, respectively.

Figure 19:
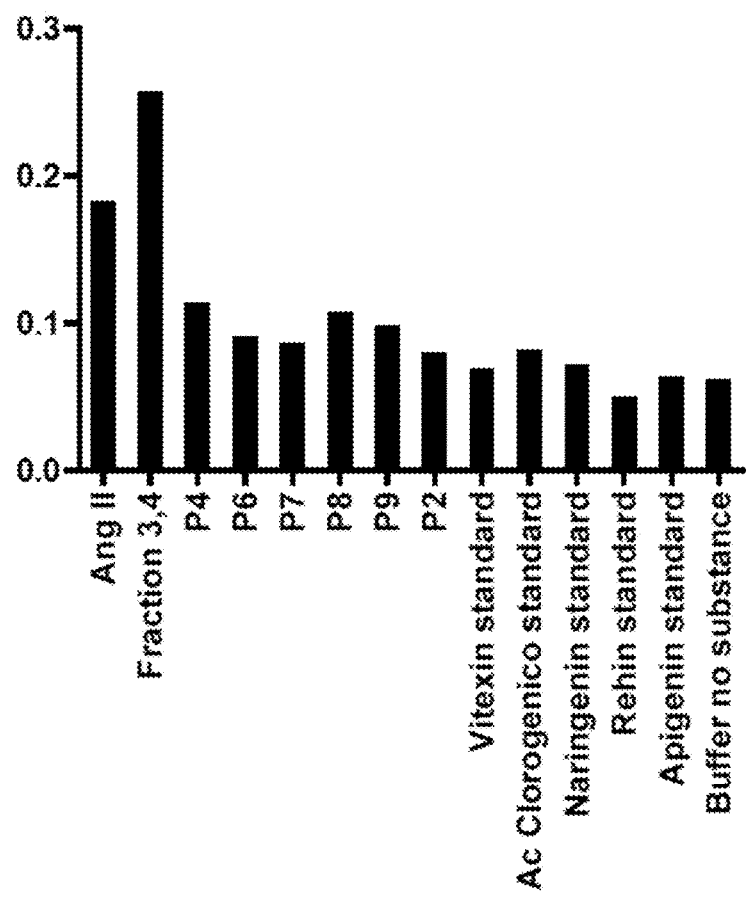
FIG. 19 is a bar graph that shows relative intracellular calcium concentrations of CHO-AEQ-AT$_2$ cells that have been exposed to various compositions.

The results are shown in FIGS. 17-19. In each figure, the Y-axis represents the amount of cytoplasmic calcium expressed as a fraction from the total intracellular content.

More particularly, FIG. 19 shows cytoplasmic calcium release after binding of the compounds or extracts to $AT_2$ receptors expressed on CHO-AEQ cells. Extract of the *Cecropia* genus containing compounds P2, P4, P6, P7, P8 and P9 showed a higher degree of activation of the $AT_2$ receptor than the $AT_2$ endogenous peptide angiotensin II. Compounds P2, P4, P6, P7, P8 and P9, individually tested, showed approximately half of the activity of the extract suggesting synergism of the individual components of *Cecropia* genus active extract on the activation of the $AT_2$ receptor.

Figure 20:
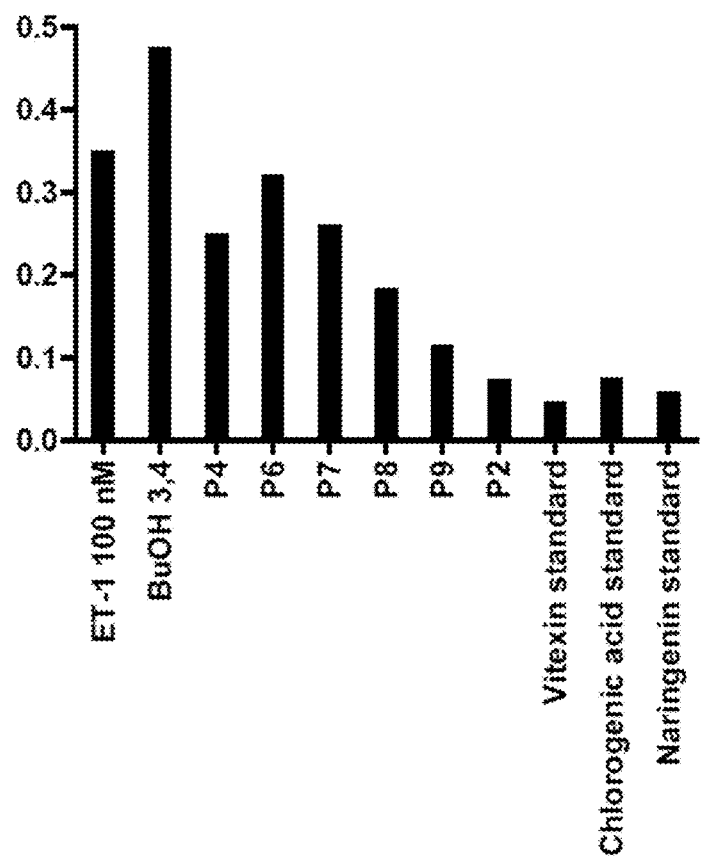
FIG. 20 is a bar graph that shows relative intracellular calcium concentrations of CHO-AEQ-ET$_B$ cells that have been exposed to various compositions.

FIG. 20 shows cytoplasmic calcium release after binding of the compounds or extracts to the $ET_B$ receptors expressed on CHO-AEQ cells. Fraction 3-4—which is composed mainly of compounds P9 and P8—induced a higher cytoplasmic calcium release than 100 nM of the endogenous agonist endothelin 1 (ET-1). In this experiment, compound P6, which is not the primary component of the extract, is the most active sample tested, followed by P4, P7, P8, P9 and P2.

Figure 21:
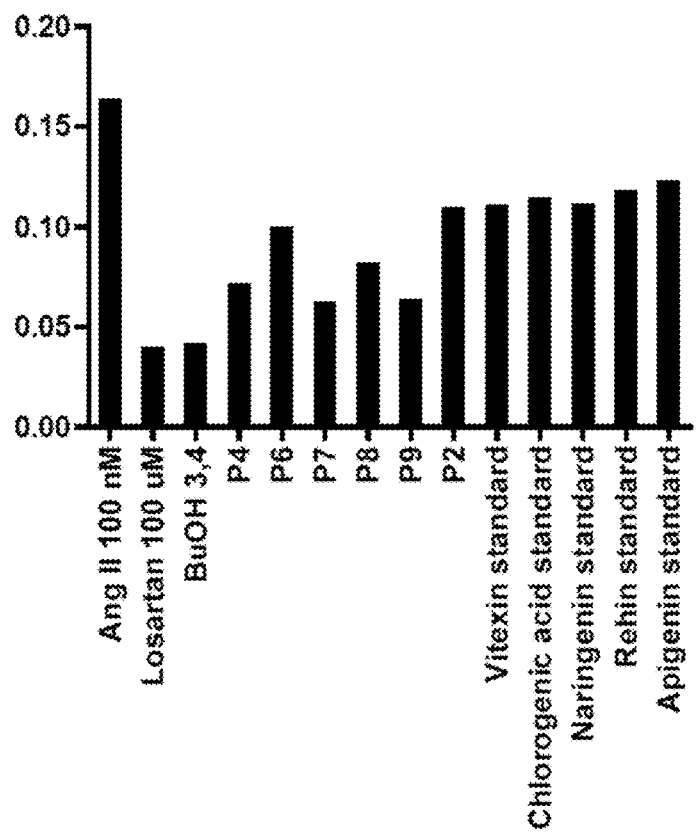
FIG. 21 is a bar graph that shows relative intracellular calcium concentrations of CHO-AEQ-AT$_1$ cells that have been exposed to various compositions.

FIG. 21 shows that Fraction 3-4 inhibits the agonistic effect of 100 nM angiotensin II on the $AT_1$ receptor with the same intensity as the selective $AT_1$ receptor antagonist losartan. Flavonoids P2, P4, P7, P8 and P9 from this fraction inhibited angiotensin II effect on the $AT_1$ receptor with different intensities. Their effect is less than half of the effect of Fraction 3-4 when tested individually, suggesting a synergistic effect of these components.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A method for producing a formulation for administration to a mammalian subject, the method comprising:
   mixing plant material with an alcohol, wherein the plant material is from one or more plants belonging to the *Cecropia* genus;
   extracting a portion of the plant material into the alcohol;
   isolating the extracted portion of plant material from a remainder of the plant material;
   removing at least a portion of the isolated extracted portion of the plant material to obtain a first composition, wherein the first composition comprises two or more flavonoids, the two or more flavonoids in the first composition being selected from the group consisting of isovitexin-2"-O-rhamnoside, isovitexin-2"-O-glucoside, isovitexin-2"-O-xyloside, isovitexin-O-xyloside, isoorientin-2"-O-xyloside, and mixtures thereof; and combining the first composition with a second composition to form the formulation for administration to the mammalian subject.

2. The method of claim 1, wherein the two or more flavonoids collectively (1) antagonize the angiotensin II receptor, type 1, (2) agonize the angiotensin II receptor, type 2, and (3) agonize the endothelin receptor type B.

3. The method of claim 1, wherein the alcohol has four or fewer carbon atoms.

4. The method of claim 1, wherein the alcohol is methanol.

5. The method of claim 1, wherein the extracted portion is further washed with a solvent comprising dichloromethane.

6. The method of claim 1, wherein the extracted portion is further washed with a solvent comprising hexane.

7. The method of claim 1, wherein the isolating the extracted portion of plant material is carried out via chromatography.

8. The method of claim 1, wherein the plant material is macerated prior to extracting a portion of the plant material into one or more organic solvents.

9. The method of claim 1, wherein the two or more flavonoids are between 0.3% and 15% of the formulation by weight.

10. The method of claim 1, wherein the plant material is exclusively from aerial parts of the plant.

11. The method of claim 1, wherein the formulation lowers blood pressure when administered to the mammalian subject.

12. The method of claim 1, wherein one or more plants belong to the species *Cecropia obtusifolia*.

13. The method of claim 1, wherein the second composition comprises a dispersant, a humectant, a carrier, an antistatic agent, a filler, a diluent, or any combination thereof.

* * * * *